(12) United States Patent
Andreyko et al.

(10) Patent No.: US 8,075,495 B2
(45) Date of Patent: Dec. 13, 2011

(54) BIOPSY DEVICES WITH UNIVERSAL PROBE

(75) Inventors: Michael J. Andreyko, Cincinnati, OH (US); John A. Hibner, Mason, OH (US); Edward A. Rhad, Fairfield, OH (US); Kyle P. Moore, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 657 days.

(21) Appl. No.: 12/141,175

(22) Filed: Jun. 18, 2008

(65) Prior Publication Data
US 2009/0318832 A1    Dec. 24, 2009

(51) Int. Cl.
*A61B 10/00*    (2006.01)
(52) U.S. Cl. .................................................. 600/567
(58) Field of Classification Search .......... 600/562–567; 604/326
See application file for complete search history.

(56) References Cited

U.S. PATENT DOCUMENTS

| | | |
|---|---|---|
| 3,994,297 A | 11/1976 | Kopf et al. |
| 5,526,822 A | 6/1996 | Burbank et al. |
| 5,775,333 A | 7/1998 | Burbank et al. |
| 5,827,305 A | 10/1998 | Gordon et al. |
| 5,928,164 A | 7/1999 | Burbank et al. |
| 5,980,469 A | 11/1999 | Burbank et al. |
| 6,086,544 A | 7/2000 | Hibner et al. |
| 6,485,436 B1 | 11/2002 | Truckai et al. |
| 6,758,824 B1 | 7/2004 | Miller et al. |
| 7,322,940 B2 | 1/2008 | Burbank et al. |
| 2003/0109801 A1 | 6/2003 | Rhad et al. |
| 2003/0109803 A1 | 6/2003 | Huitema et al. |
| 2005/0159677 A1 | 7/2005 | Shabaz et al. |
| 2006/0074344 A1 | 4/2006 | Hibner |
| 2006/0144548 A1 | 7/2006 | Beckman et al. |
| 2007/0032740 A1 | 2/2007 | Quick et al. |
| 2007/0032742 A1 | 2/2007 | Monson et al. |
| 2007/0118048 A1 | 5/2007 | Stephens et al. |
| 2008/0195066 A1* | 8/2008 | Speeg et al. .................... 604/326 |

FOREIGN PATENT DOCUMENTS

| | | |
|---|---|---|
| EP | 1 433 423 | 6/2004 |
| WO | WO 2004/084738 | 10/2004 |

OTHER PUBLICATIONS

U.S. Appl. No. 11/942,764, filed Nov. 20, 2007, Hibner.
U.S. Appl. No. 11/942,785, filed Nov. 27, 2007, Hibner.
U.S. Appl. No. 11/964,811, filed Dec. 27, 2007, Hibner.

(Continued)

*Primary Examiner* — Brian Szmal
(74) *Attorney, Agent, or Firm* — Frost Brown Todd LLC

(57) ABSTRACT

A biopsy device comprises a probe that is configured to couple with a holster. The probe comprises a needle, a cutter, and a body portion. The needle is rotatable and translatable relative to the body portion. The holster has a locking feature that is configured to prevent the needle from rotating relative to the body portion upon coupling of the probe with the holster. The locking feature may also be configured to prevent the needle from translating relative to the body portion upon coupling of the probe with the holster. The same probe may thus be used with a holster intended for use in a fixture-based, stereotactic setting, in which rotation and translation of the needle may be desired; and with a holster intended for use in a handheld, ultrasound-guided setting, in which rotation and translation of the needle may be less desired if not undesirable.

20 Claims, 21 Drawing Sheets

OTHER PUBLICATIONS

U.S. Appl. No. 11/965,048, filed Dec. 27, 2007, Hibner.
U.S. Appl. No. 11/942,764, filed Nov. 20, 2007, Ritchie et al.
U.S. Appl. No. 11/952,393, filed Dec. 7, 2007, Ritchie et al.
U.S. Appl. No. 11/952,405, filed Dec. 7, 2007, Hibner et al.
U.S. Appl. No. 11/965,048, filed Dec. 27, 2007, Hibner et al.
U.S. Appl. No. 12/038,359, filed Feb. 27, 2008, Speeg et al.
European Search Report dated Aug. 31, 2009 for Application No. 09251576.
European Search Report dated May 18, 2006 for Application No. EP 05256053.

* cited by examiner

BIOPSY DEVICES WITH UNIVERSAL PROBE

BACKGROUND

Biopsy samples have been obtained in a variety of ways in various medical procedures using a variety of devices. Biopsy devices may be used under stereotactic guidance, ultrasound guidance, MRI guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; and U.S. Provisional Patent Application Ser. No. 60/874,792, entitled "Biopsy Sample Storage," filed Dec. 13, 2006; and U.S. Non-Provisional patent application Ser. No. 11/942,764, entitled "Vacuum Timing Algorithm for Biopsy Device," filed Nov. 20, 2007. The disclosure of each of the above-cited U.S. patents, U.S. patent application Publications, U.S. Provisional Patent Applications, and U.S. Non-Provisional patent application is incorporated by reference herein.

Some biopsy systems may provide one particular type of device or devices for use in handheld, ultrasound-guided settings; with another particular type of device or devices for use in a fixture-based, stereotactic settings. Such differing devices for different settings may not permit interchangeability of components from devices of one setting to devices of another setting. For instance, one biopsy system may provide a holster and probe pair intended for use in a handheld, ultrasound-guided setting, and a separate holster and probe pair intended for use in a fixture-based, stereotactic setting, without permitting the probe of the first pair to be effectively coupled with the holster of the second pair. In some situations, it might be desirable to permit the same type of probe to be effectively coupled with a holster intended for use in a handheld, ultrasound-guided setting as well as a holster intended for use in a fixture-based, stereotactic setting.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
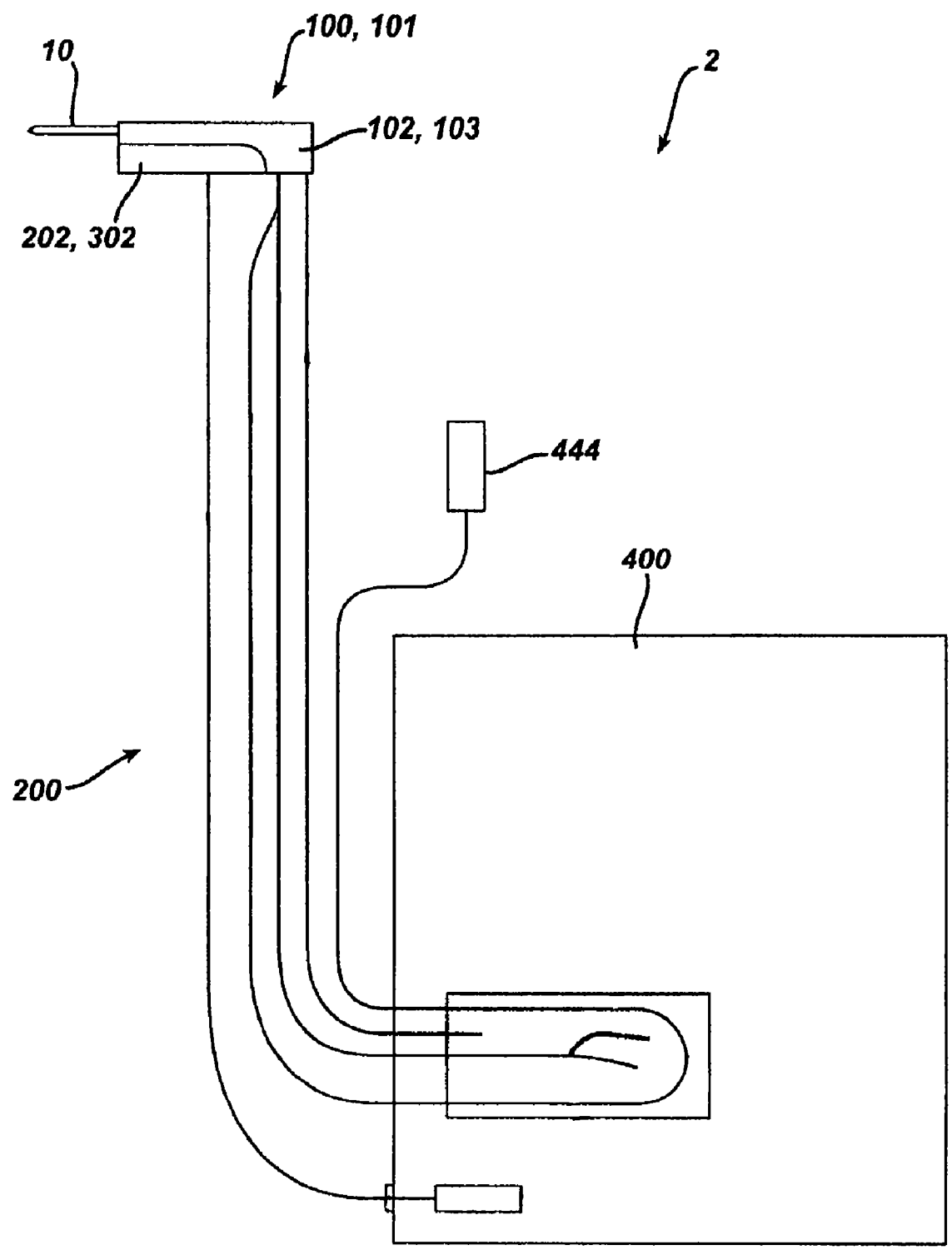
FIG. 1 depicts a schematic view of an exemplary biopsy system.
Figure 2:
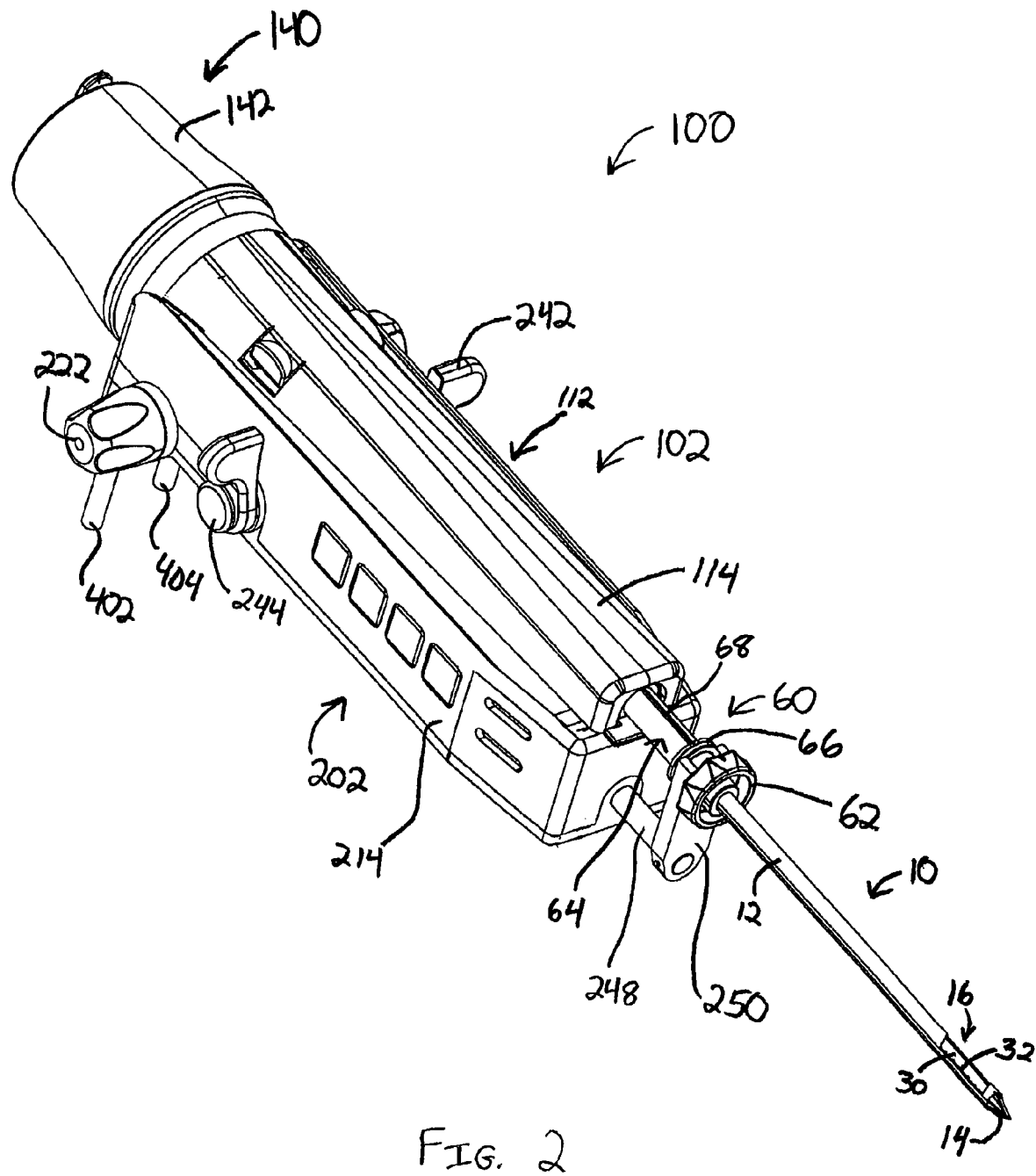
FIG. 2 depicts a perspective view of an exemplary assembled biopsy device, for use in a stereotactic setting.
Figure 3:
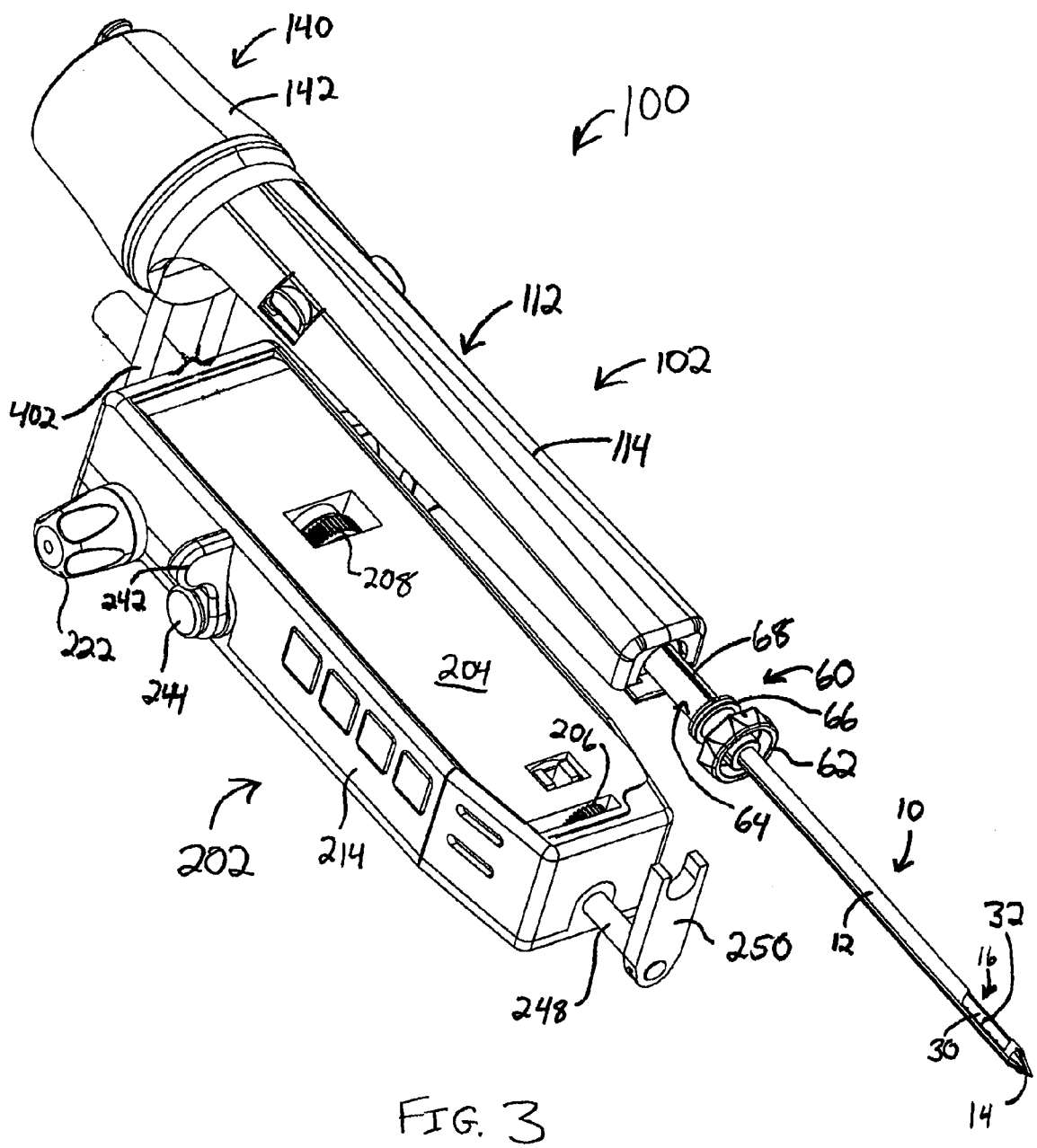
FIG. 3 depicts an exploded view of the biopsy device of FIG. 2, with the probe detached from the holster.
Figure 4:
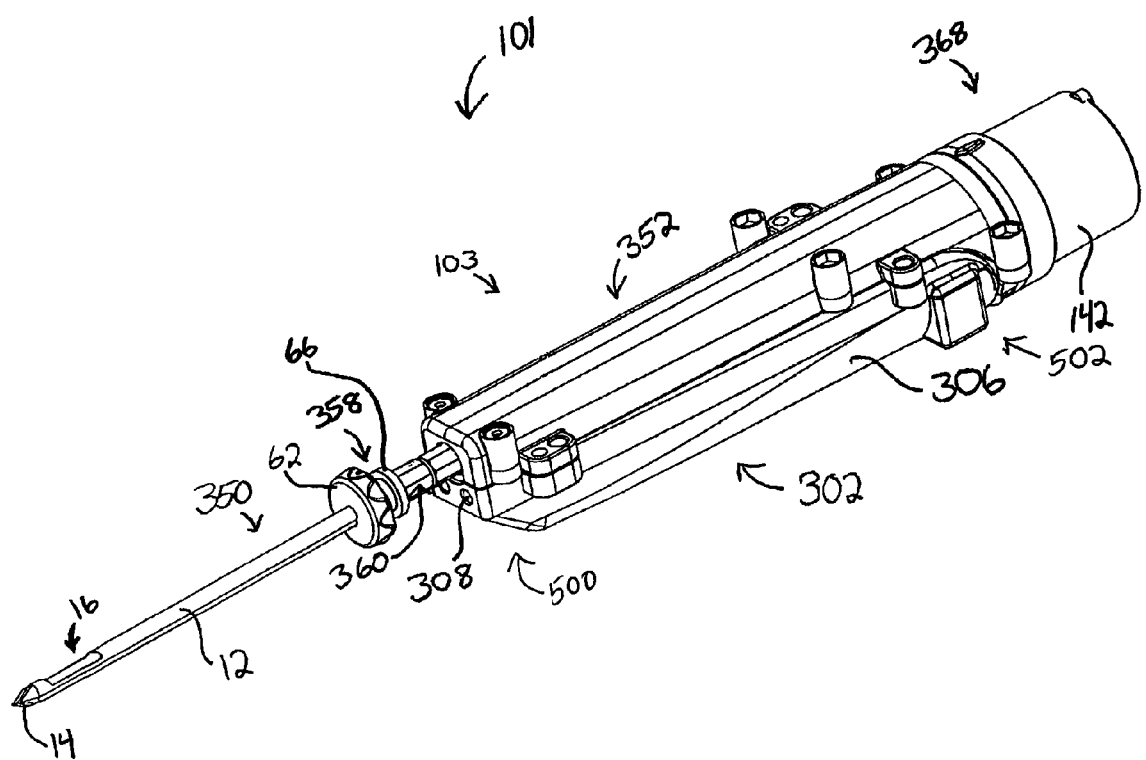
FIG. 4 depicts a perspective view of an exemplary assembled biopsy device, for use in an ultrasound setting.
Figure 5:
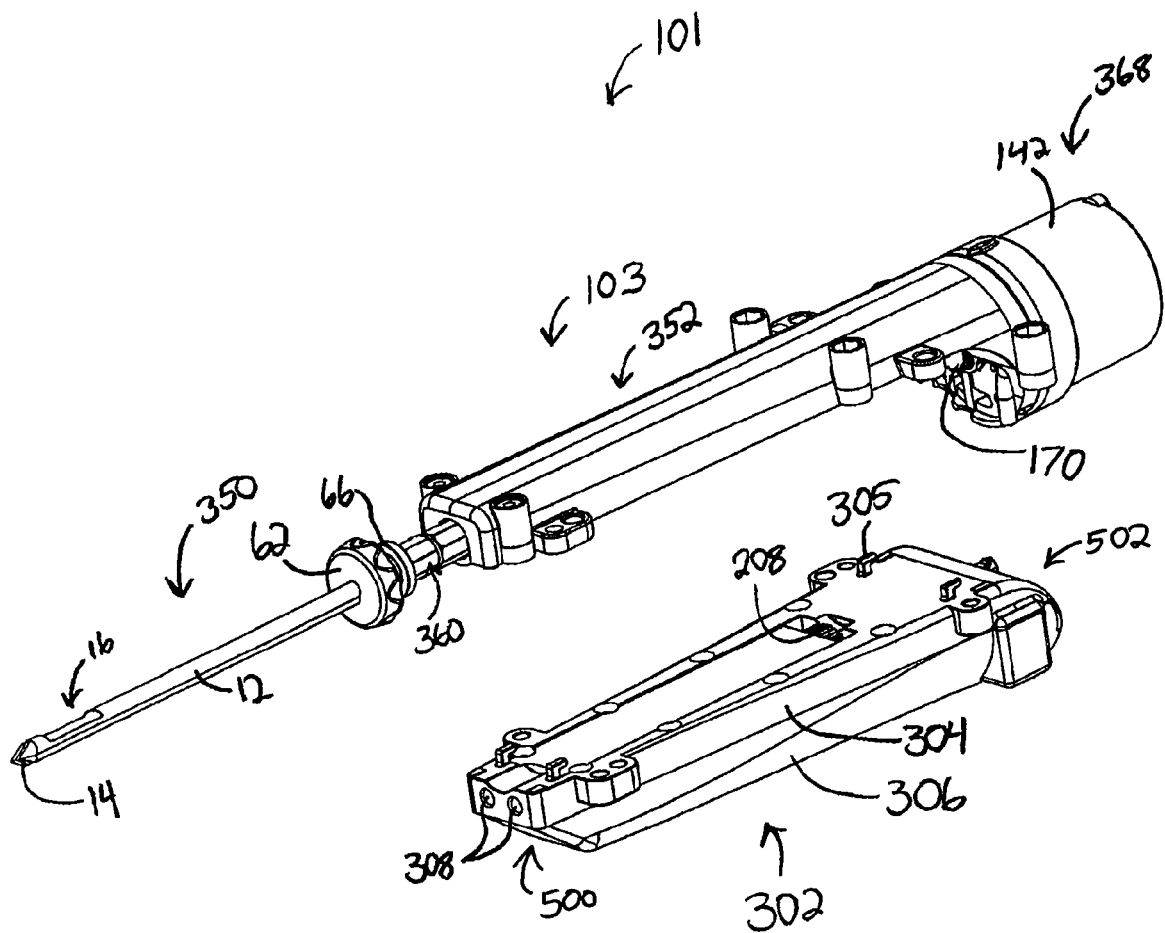
FIG. 5 depicts an exploded view of the biopsy device of FIG. 4, with the probe detached from the holster.
Figure 6:
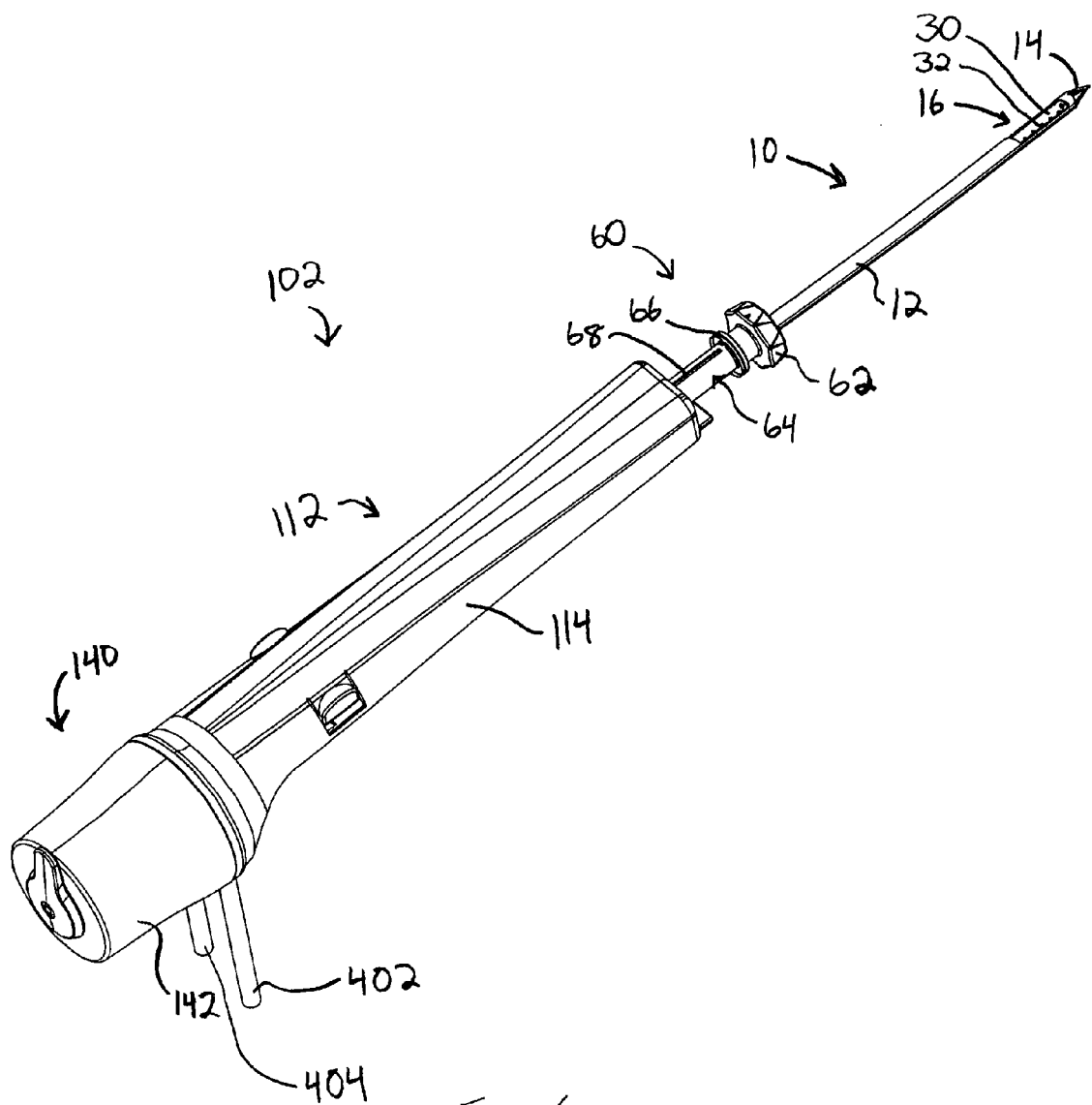
FIG. 6 depicts a top perspective view of a probe portion of the biopsy device of FIG. 2.
Figure 7:
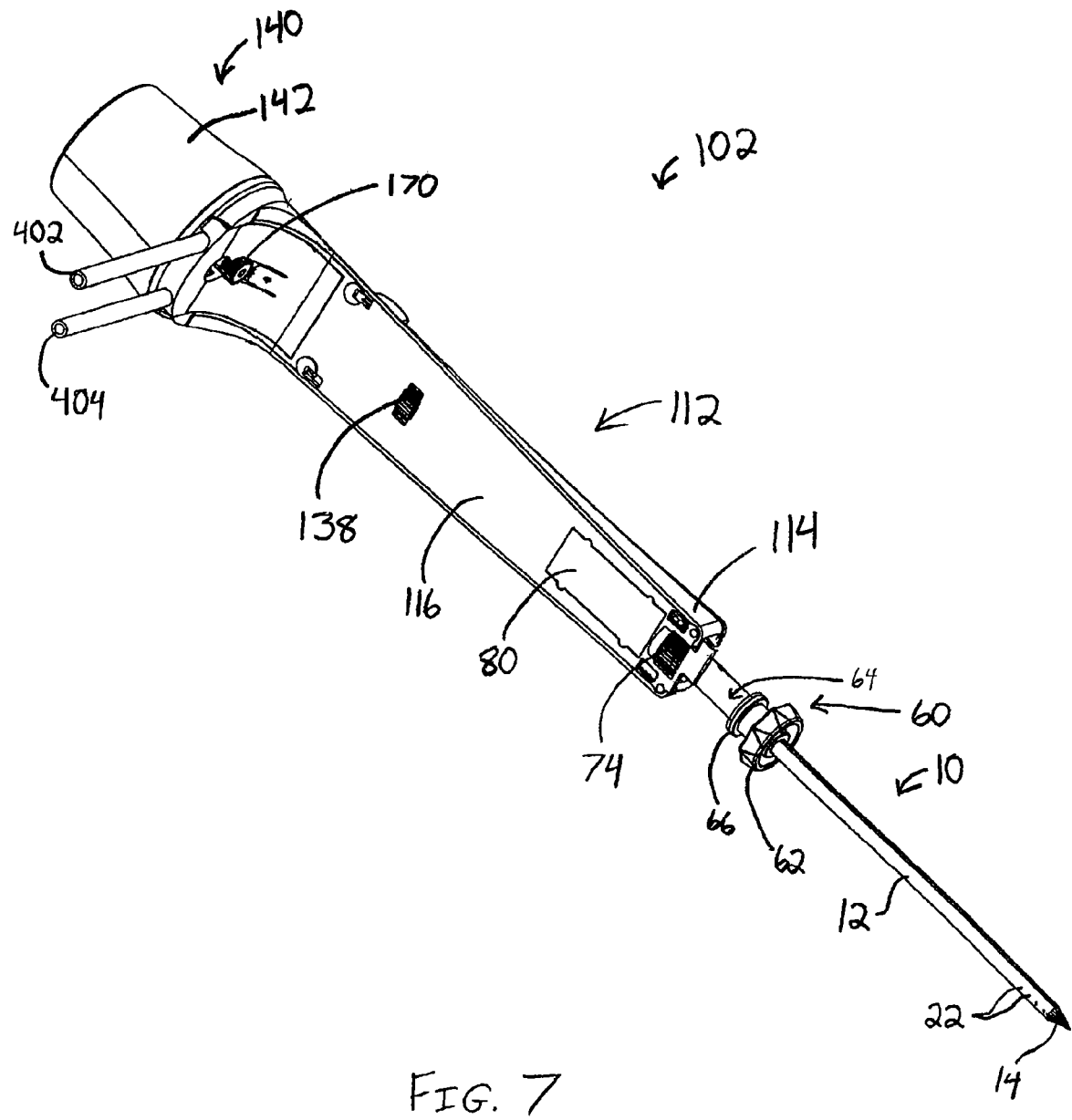
FIG. 7 depicts a bottom perspective view of the probe portion of FIG. 6.
Figure 8:
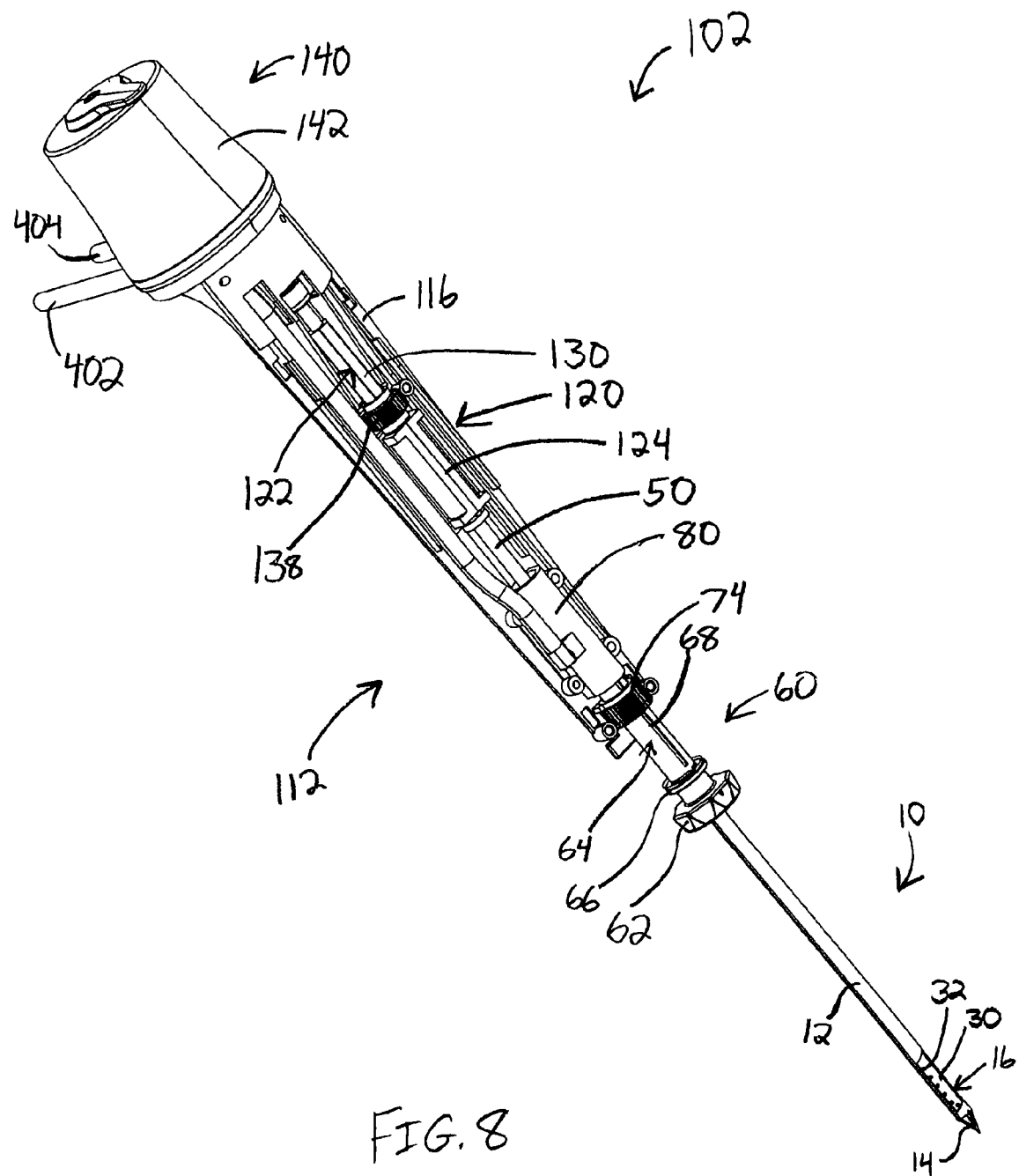
FIG. 8 depicts a top perspective view of the probe portion of FIG. 6, with a top cover removed.
Figure 9:
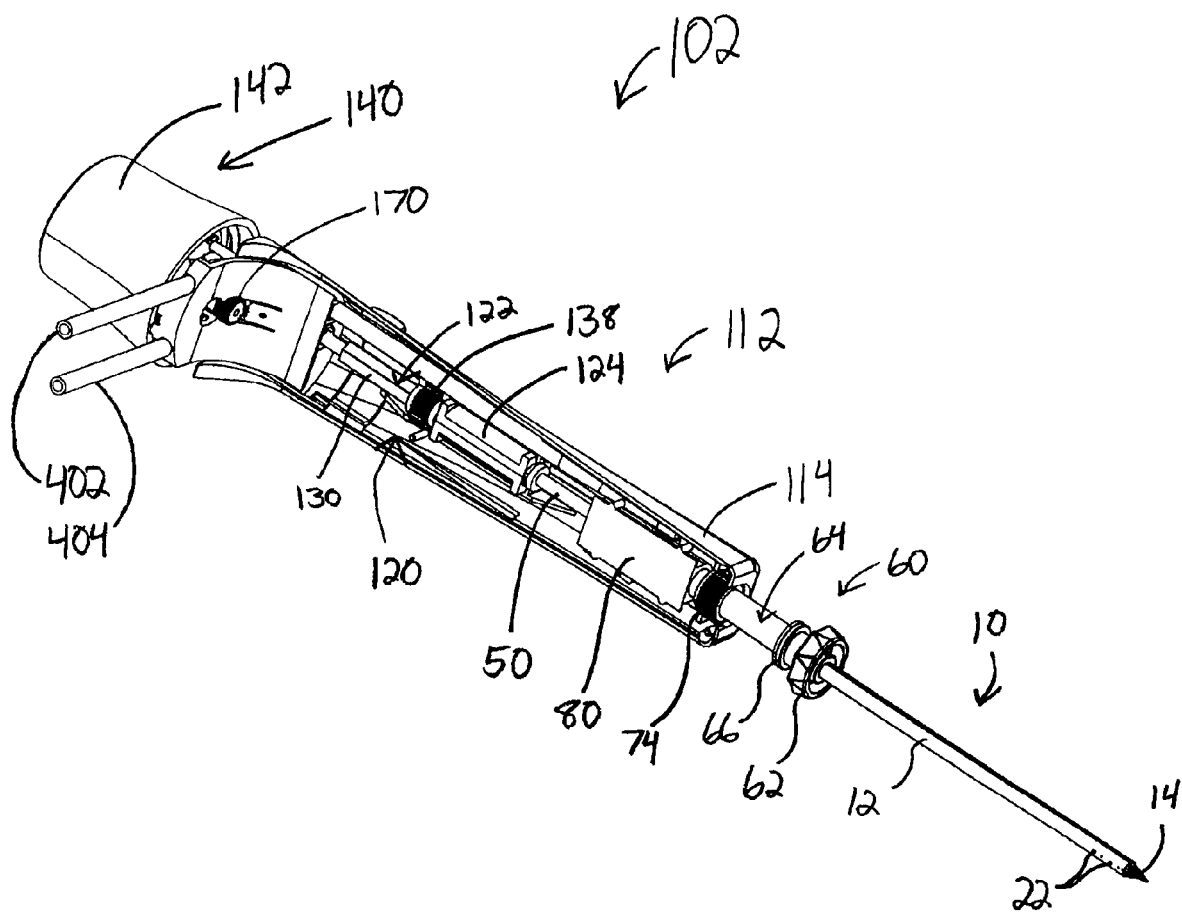
FIG. 9 depicts a bottom perspective view of the probe portion of FIG. 6, with a base removed.

As shown in FIG. 1, an exemplary biopsy system (2) includes a biopsy device (100, 101) and a vacuum control module (400). As shown in FIGS. 2-3, biopsy device (100) comprises a probe (102) and a holster (202). Similarly, as shown in FIGS. 4-5, biopsy device (101) comprises a probe (103) and a holster (302). As will be described in greater detail below, each probe (102, 103) is separable from its corresponding holster (202, 302). Use of the term "holster" herein should not be read as requiring any portion of probe (102, 103) to be inserted into any portion of holster (202, 302). Indeed, in some variations of biopsy devices (100, 101), probe (102, 103) may simply sit on holster (202, 302). In some other variations, a portion of holster (202, 302) may be inserted into probe (102, 103). Furthermore, in some biopsy devices (100, 101), probe (102, 103) and holster (202, 302) may be of unitary or integral construction, such that the two components cannot be separated. Still other suitable structural and functional relationships between probe (102, 103)

and holster (202, 302) will be apparent to those of ordinary skill in the art in view of the teachings herein.

By way of example only, probe (102, 103) may be provided as a disposable component, while holster (202, 302) may be provided as a reusable component. Vacuum control module (400) is provided on a cart (not shown) in the present example, though like other components described herein, a cart is merely optional. Among other components described herein, a footswitch (not shown) and/or other devices may be used to provide at least some degree of control of at least a portion of biopsy system (2). Conduits (200) provide communication of power (e.g., electrical, pneumatic, etc.), control signals, saline (e.g., provided by a saline bag (444)), vacuum, and venting from vacuum control module (400) to biopsy device (100, 101). Any of these components may be provided and operated in accordance with the teachings of U.S. Non-Provisional patent application Ser. No. 11/942,764, entitled "Vacuum Timing Algorithm for Biopsy Device," filed Nov. 20, 2007, the disclosure of which is incorporated by reference herein.

I. Exemplary Probe for Stereotactic Use

As shown in FIGS. 2-3 and 6-13, probe (102) comprises a needle portion (10) and a body portion (112). Body portion (112) comprises a cover member (114) and a base member (116). A tissue sample holder (140) is removably secured to base member (116), though tissue sample holder (140) may alternatively be secured to cover member (114) or some other component. A pair of tubes (402, 404) are coupled with probe (102) to provide communication of fluid (e.g., vacuum, atmospheric air, pressurized air, saline, etc.) to probe (102).

Several components of probe (102) will be described in greater detail below. Other suitable components of, variations of, and uses for a probe (102) are described in U.S. Non-Provisional patent application Ser. No. 11/942,764, entitled "Vacuum Timing Algorithm for Biopsy Device," filed Nov. 20, 2007, the disclosure of which is incorporated by reference herein.

A. Exemplary Needle and Cutter

In the present example, needle portion (10) comprises an outer cannula (12) having a tissue piercing tip (14) and a transverse tissue receiving aperture (16) located proximally from the tissue piercing tip (14). In some versions, tip (14) comprises any one of the biopsy device needle tips disclosed in U.S. Provisional Application Ser. No. 60/917,375, filed May 11, 2007, entitled "Biopsy Device Needle Tip," the disclosure of which is incorporated by reference herein. Alternatively, tip (14) may comprise any one of the biopsy device needle tips disclosed in U.S. Non-Provisional application Ser. No. 12/038,359, filed Feb. 27, 2008, entitled "Needle Tip for Biopsy Device," the disclosure of which is incorporated by reference herein, or any other type of needle tip.

The interior of outer cannula (12) of the present example defines a cannula lumen (20) and a vacuum lumen (40), with a wall (30) separating the cannula lumen (20) from the vacuum lumen (40). A plurality of external openings (22) are formed in outer cannula (12), and are in fluid communication with the vacuum lumen (40). Examples of openings that are similar to external openings (22) are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, external openings (22) are merely optional. The wall (30) between the cannula lumen (20) and the vacuum lumen (40) also has a plurality of openings (32) permitting fluid communication between the cannula lumen (20) and the vacuum (40) lumen in the present example, though such openings (32) are also merely optional.

Other features that needle portion (10) may have may include any of those described in U.S. Non-Provisional patent application Ser. No. 11/942,764, entitled "Vacuum Timing Algorithm for Biopsy Device," filed Nov. 20, 2007, the disclosure of which is incorporated by reference herein.

Figure 10:
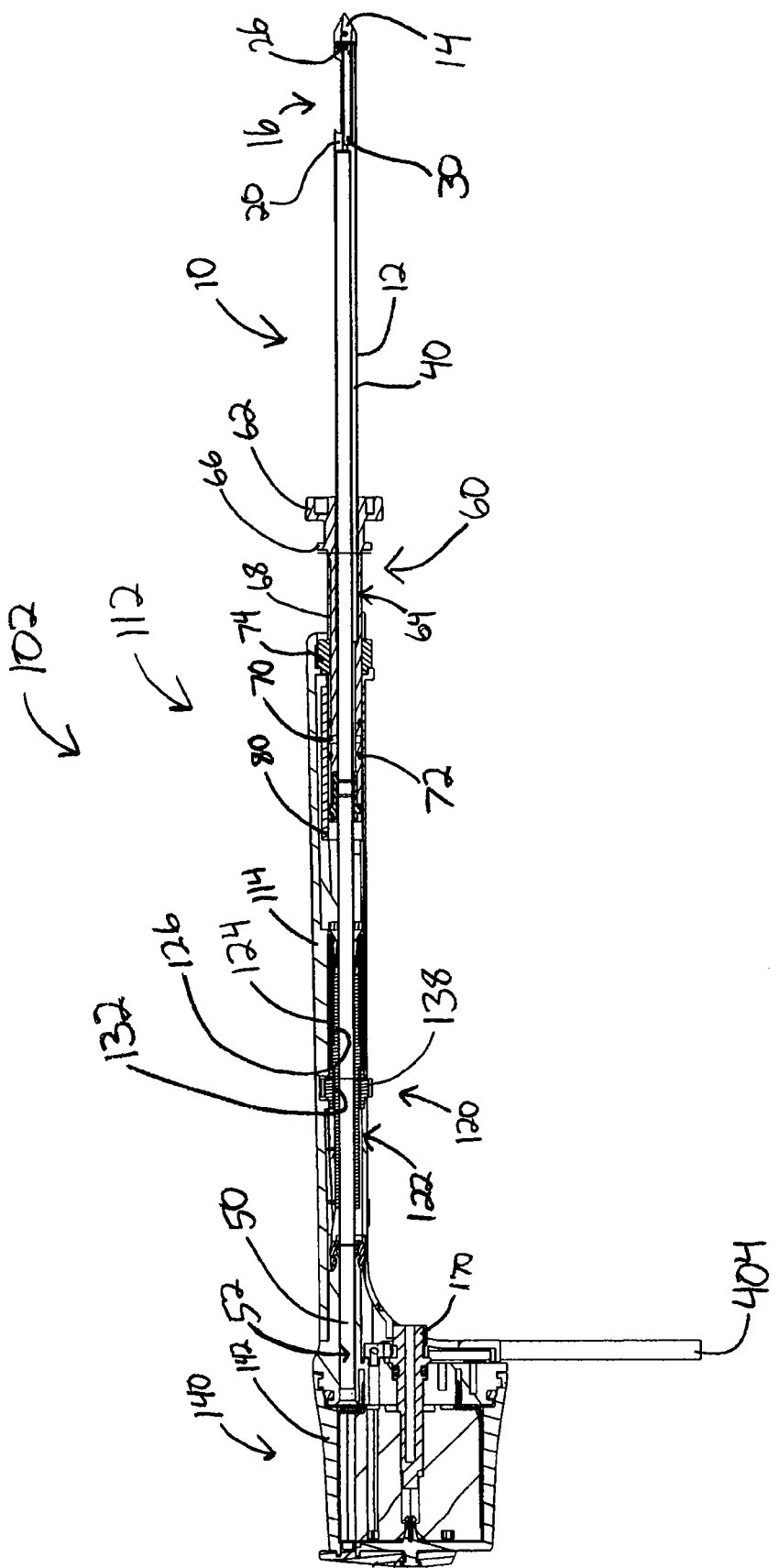
FIG. 10 depicts a lateral cross-sectional view of the probe portion of FIG. 6, taken along a longitudinal plane.

As shown in FIG. 10, a hollow cutter (50) is disposed within cannula lumen (20). The interior of cutter (50) defines a cutter lumen (52), such that fluid and tissue may be communicated through cutter (50) via cutter lumen (52). As will be described in greater detail below, cutter (50) is configured to rotate within cannula lumen (20) and translate axially within cannula lumen (20). In particular, cutter (50) is configured to sever a biopsy sample from tissue protruding through transverse aperture (16) of outer cannula (12). As will also be described in greater detail below, cutter (50) is further configured to permit severed tissue samples (4) to be communicated proximally through cutter lumen (52). Merely illustrative examples of such severing and proximal communication are described in U.S. Pat. No. 5,526,822, the disclosure of which is incorporated by reference herein, though any other suitable structures or techniques may be used for severing and/or communicating tissue samples (4) within a biopsy system (2).

In addition, suitable components of, variations of, structures for, relationships between, and configurations for cannula (12) and a cutter (50) are disclosed in U.S. Non-Provisional patent application Ser. No. 11/942,764, entitled "Vacuum Timing Algorithm for Biopsy Device," filed Nov. 20, 2007, the disclosure of which is incorporated by reference herein. Of course, any other suitable components, structures, variations, or configurations may be used.

B. Exemplary Needle Hub

Figure 11:
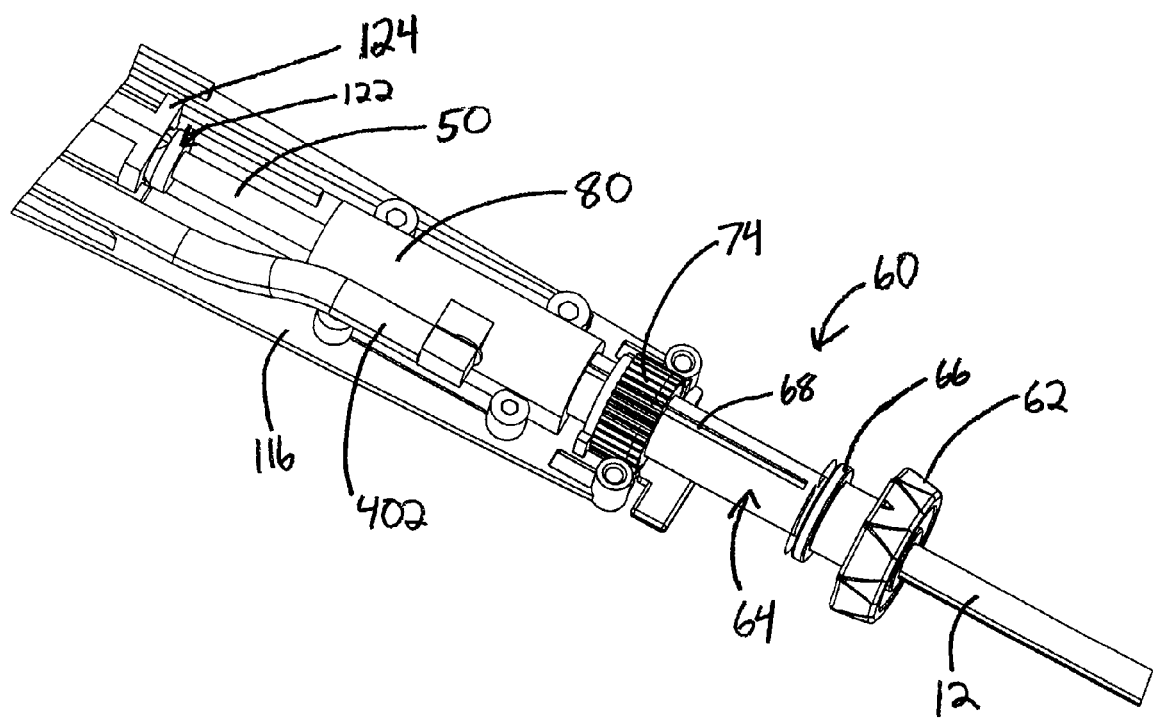
FIG. 11 depicts a partial perspective view of the probe portion of FIG. 6, showing a needle hub assembly.
Figure 12:
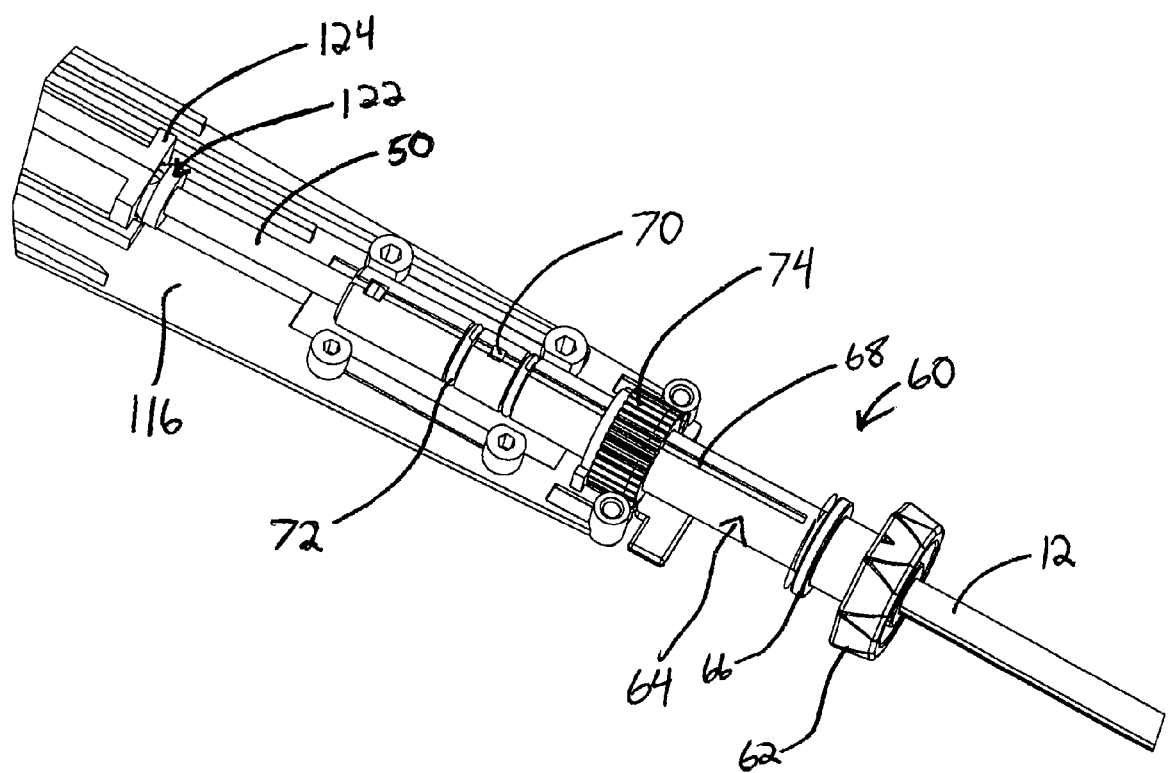
FIG. 12 depicts a partial perspective view of the probe portion of FIG. 6, showing a needle hub assembly with a needle manifold removed.
Figure 13:
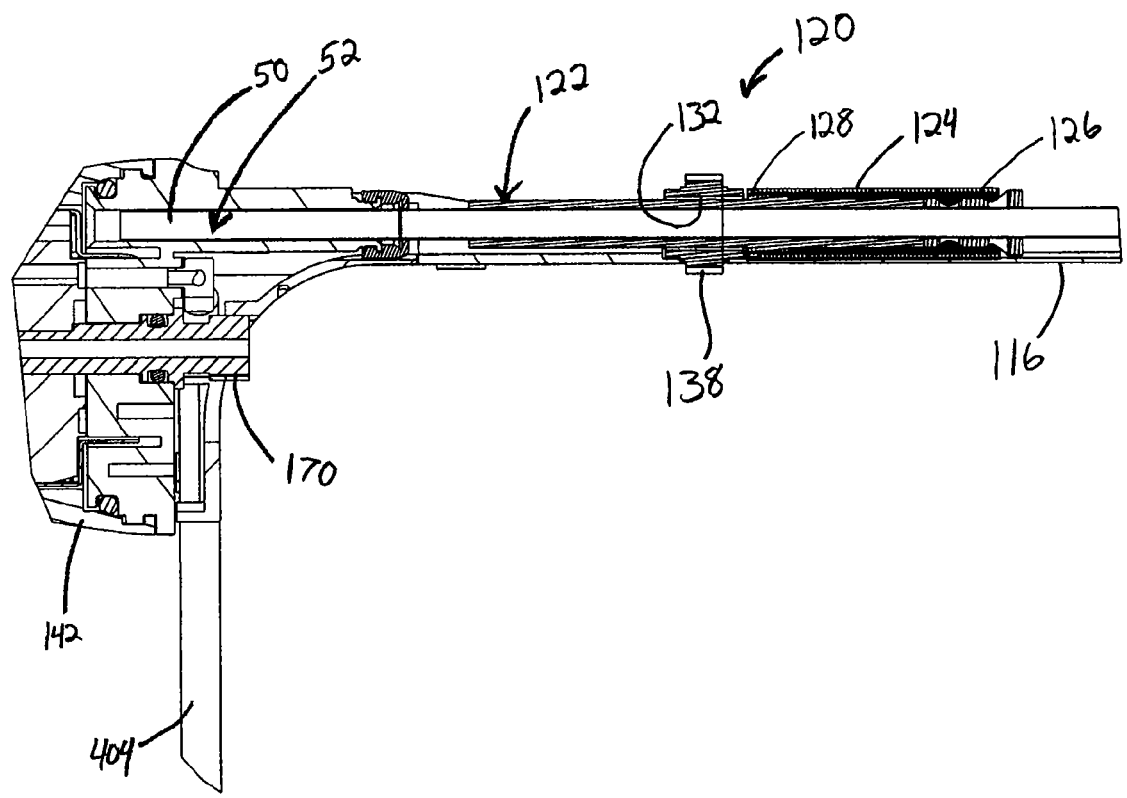
FIG. 13 depicts a partial, cross-sectional view of a cutter rotation and translation mechanism of the probe portion of FIG. 6, taken along a longitudinal plane.

As shown in FIGS. 11-12, a needle hub (60) is secured to outer cannula (12), and comprises a thumbwheel (62) and a sleeve portion (64) extending proximally from thumbwheel (62). Needle hub (60) of the present example is overmolded about a proximal portion of outer cannula (12), though needle hub (60) may be formed and/or secured relative to outer cannula (12) using any other suitable techniques (e.g., set screws, adhesives, etc.). Furthermore, while needle hub (60) of the present example is formed of a plastic material, any other suitable material or combination of materials may be used.

Sleeve portion (64) of the present example comprises an annular projection (66), a longitudinal slot (68), and a transverse opening (70), which is formed near the proximal end of sleeve portion (64). One or more additional transverse openings (70) (e.g., diametrically opposed transverse openings (70)) may also be provided in sleeve portion (64). A pair of o-rings (72) are positioned such that one o-ring (72) is proximal to transverse opening (70) and another o-ring (72) is distal to transverse opening (70). As will be described in greater detail below, transverse opening (70) is in fluid communication with the interior defined by needle hub (60), which is also in fluid communication with vacuum lumen (40) of outer cannula (12). Other suitable configurations for sleeve portion (64) will be apparent to those of ordinary skill in the art in view of the teachings herein.

Thumbwheel (62) is operable to rotate outer cannula (12) about its longitudinal axis, relative to cover member (114) and base member (116). For instance, thumbwheel (62) may be used to orient aperture (16) to a number of desired orientations about the longitudinal axis defined by outer cannula (12). Such multiple orientations may be desirable, by way of example only, to obtain a plurality of tissue samples (4) from a biopsy site, without requiring the needle portion (10) to be removed from the patient during the acquisition of such a plurality of tissue samples (4). An illustrative example of such rotation and acquisition of multiple tissue samples (4) is disclosed in U.S. Pat. No. 5,526,822, the disclosure of which is incorporated by reference herein. Other ways in which multiple tissue samples (4) may be obtained at various locations will be apparent to those of ordinary skill in the art in view of the teachings herein. For instance, rotation of outer cannula (12) may be motorized or automated, such as using any of the components described in greater detail below, or using any other suitable components or techniques. As another non-exhaustive example, an entire biopsy device (101) may be rotated during acquisition of tissue samples (4), without necessarily removing biopsy device (101) from the patient during such rotation and tissue sample (4) acquisition, to obtain tissue samples (4) from various orientations about the longitudinal axis defined by outer cannula (12).

It will also be appreciated that other structures may be used to perform manual rotation of outer cannula (12). In particular, and as shown in FIGS. 11-12, an exposed gear (74) may be engaged with outer cannula (12). In this example, gear (74) is slid onto the proximal end of sleeve portion (64). A radially inwardly extending projection (not shown) of gear (74) is configured to mate with slot (68) of sleeve portion (64), such that gear (74) rotates unitarily with sleeve portion (64) while being movable longitudinally along sleeve portion (64). With sleeve portion (64) being unitarily engaged with outer cannula (12), rotation of gear (74) will further cause rotation of cannula (12) for reorienting aperture (16). Gear (74) is further configured to engage with a complementary exposed gear (206) of holster (202), as will be described in greater detail below. In particular, gear (74) is configured to mesh with gear (206) such that gear (206) can impart rotation to gear (74), thereby rotating outer cannula (12). Some exemplary structures and techniques for selectively causing gear (206) to rotate are described in U.S. Non-Provisional patent application Ser. No. 11/942,764, entitled "Vacuum Timing Algorithm for Biopsy Device," filed Nov. 20, 2007, the disclosure of which is incorporated by reference herein, while others will be apparent to those of ordinary skill in the art in view of the teachings herein.

C. Exemplary Needle Manifold

As shown in FIGS. 8-11, a needle manifold (80) is provided about sleeve portion (64). Needle manifold (80) is fixed relative to base member (116) in this example. Needle manifold (80) is in fluid communication with tube (402), such that tube (402) may communicate saline, a vacuum, atmospheric air, and/or pressurized air, etc., to needle manifold (80). Needle manifold (80) is further in fluid communication with the interior of sleeve portion (64), via transverse opening (70), which is shown in FIG. 12. O-rings (72) are configured to maintain a fluid seal between needle manifold (80) and sleeve portion (64), even as sleeve portion (64) translates longitudinally relative to needle manifold (80), such as during firing of needle (10) as will be described in greater detail below; and even during rotation of sleeve portion (64) about its longitudinal axis. A seal (not shown) is also provided at the proximal end of sleeve portion (64), at the interface between sleeve portion (64) and cutter (50). Needle manifold (80), sleeve portion (64), and outer cannula (12) are thus configured and arranged such that saline, a vacuum, atmospheric air, and/or pressurized air, etc. that is communicated via tube (402) to needle manifold (80) will be communicated to vacuum lumen (40) via transverse opening (70). Of course, any other suitable structures or arrangements may be used to communicate saline, a vacuum, atmospheric air, and/or pressurized air, etc. from tube (402) to vacuum lumen (40).

D. Exemplary Cutter Rotation and Translation Mechanism

In the present example, and as shown in FIGS. 8-10 and 13, body portion (112) of probe (102) comprises a cutter rotation and translation mechanism (120), which is operable to rotate and translate cutter (50) within outer cannula (12). Cutter rotation and translation mechanism (120) comprises a sleeve (122) unitarily secured to cutter (50), a nut member (124), and a gear (138). Nut member (124) is secured relative to base member (116), and has internal threads (126). A portion of sleeve (122) has external threads (128) that are configured to engage with threads (126) of nut member (124). Threads (126, 128) are configured such that, as sleeve (122) rotates relative to nut member (124), sleeve (122) will longitudinally translate relative to nut member (124), depending on the direction of such relative rotation.

Another portion of sleeve (122) has a plurality of external flats (130), which are configured to engage with a complementary plurality of internal flats (132) of gear (138). Gear (138) is positioned coaxially about sleeve (122) and cutter (50). Flats (130, 132) are configured such that rotation of gear (138) causes rotation of sleeve (122). With sleeve (122) being unitarily secured to cutter (50) in the present example, rotation of gear (138) and sleeve (122) will result in the same rotation of cutter (50). Flats (130, 132) are further configured such that sleeve (122) may translate longitudinally relative to gear (138) (e.g., the fit between sleeve (122) and gear (138) is not so tight as to prevent such translation). It will therefore be appreciated that, as gear (138) rotates, given the relative configurations of threads (126, 128) and flats (130, 132), such rotation of gear (138) will simultaneously result in rotation and longitudinal translation of sleeve (122), which will in turn result in simultaneous rotation and longitudinal translation of cutter (50).

In the present example, gear (138) is partially exposed through base member (116), and is configured to mate with a complementary exposed gear (208) of holster (202). In particular, gear (138) is configured to mesh with gear (208) such that gear (208) can impart rotation to gear (138), thereby activating cutter rotation and translation mechanism (120). Gear (208) is in communication with a motor that is within holster (202). Of course, any other components may be used to provide of cutter (50) translation and/or rotation.

Other suitable components and features that may be used with a cutter rotation and translation mechanism (120) are disclosed in U.S. Non-Provisional patent application Ser. No. 11/942,764, entitled "Vacuum Timing Algorithm for Biopsy Device," filed Nov. 20, 2007, the disclosure of which is incorporated by reference herein.

F. Exemplary Tissue Sample Holder

Figure 14:
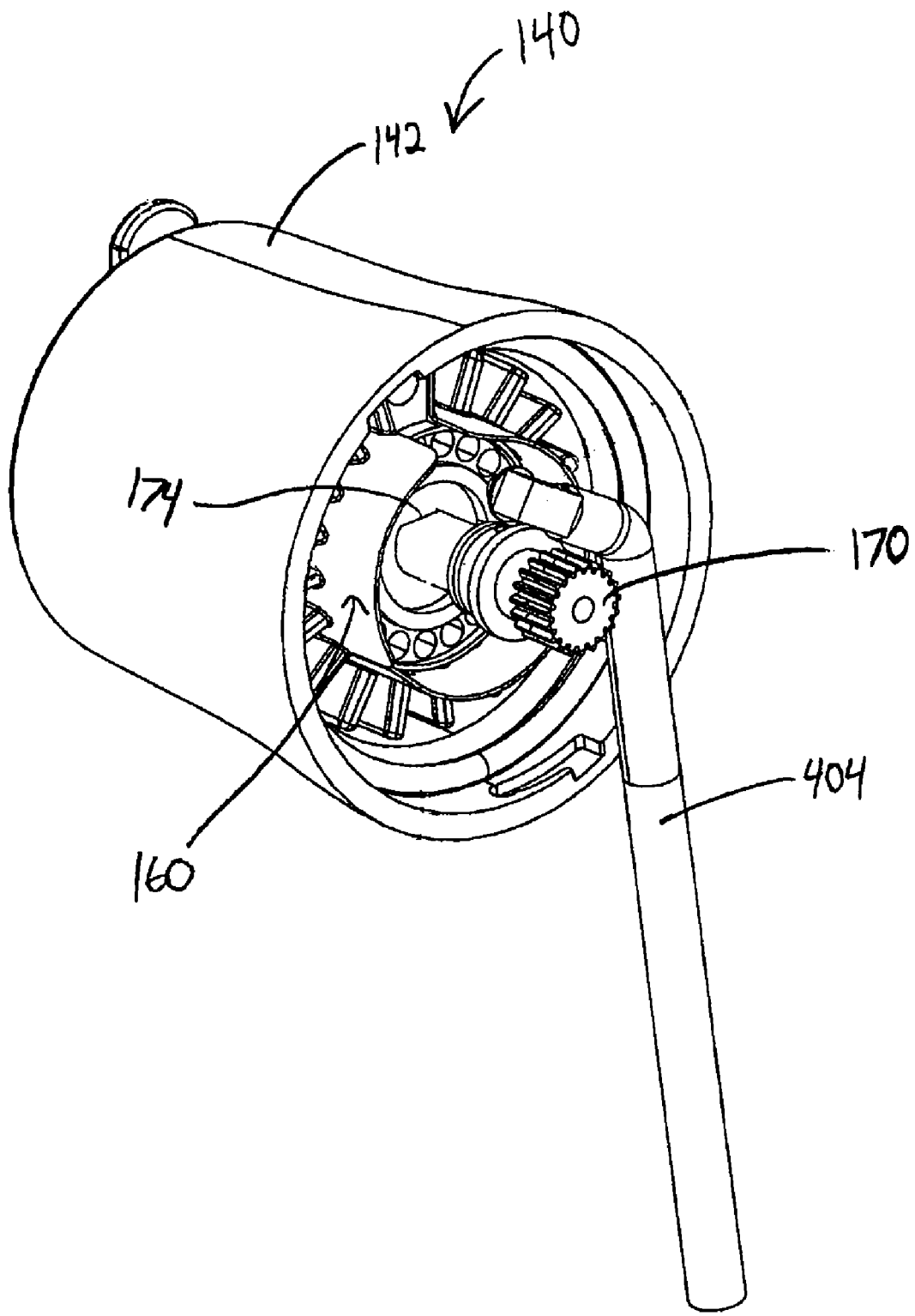
FIG. 14 depicts a front perspective view of an exemplary tissue sample holder.

In the present example, a tissue sample holder (140) is provided at the end of body portion (112) of probe (102). As shown in FIG. 14, tissue sample holder (140) comprises a cup (142), a rotatable manifold (174), and a plurality of removable sample trays (160) with a plurality of tissue sample chambers (not shown). Each tissue sample chamber is configured to separately hold a tissue sample communicated proximally through the cutter lumen (20), such that tissue sample holder (140) may separately hold a plurality of tissue samples. In particular, the manifold (174) is configured to rotate, by rotation of gear (170), to selectively index a tissue sample chamber relative to the cutter lumen (20). Manifold (174) is further configured to communicate a vacuum from tube (404) to the cutter lumen (20), regardless of which tissue sample chamber is indexed relative to the cutter lumen (20). Suitable components and structures for and methods of operating a tissue sample holder (140) are disclosed in U.S. Non-Provisional patent application Ser. No. 11/942,764, entitled "Vacuum Timing Algorithm for Biopsy Device," filed Nov. 20, 2007, the disclosure of which is incorporated by reference herein. Of course, any other suitable components, structures, or configurations may be used.

II. Exemplary Holster for Stereotactic Use

Figure 15:
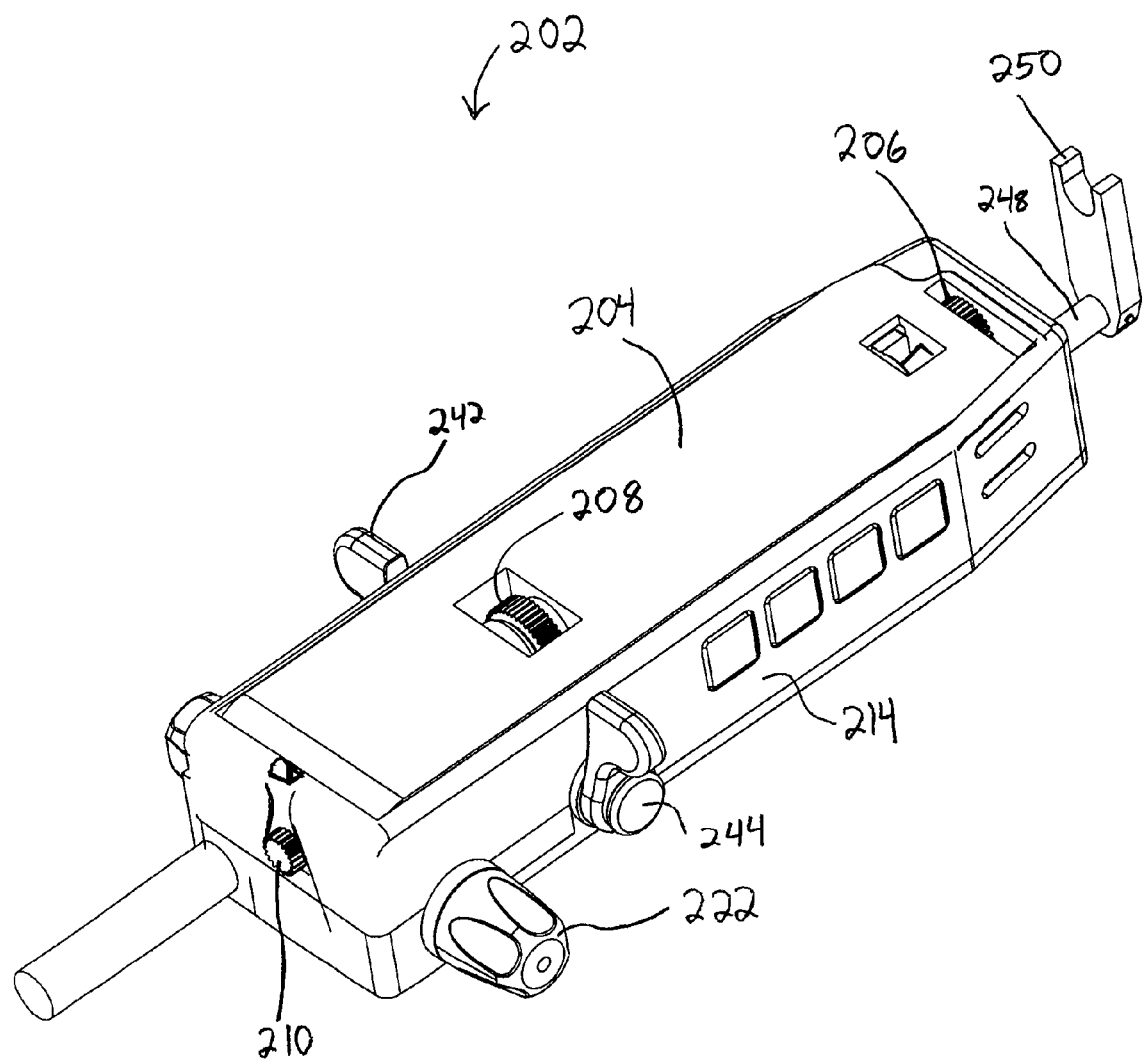
FIG. 15 depicts a perspective view of a holster of the biopsy device of FIG. 2.
Figure 16:
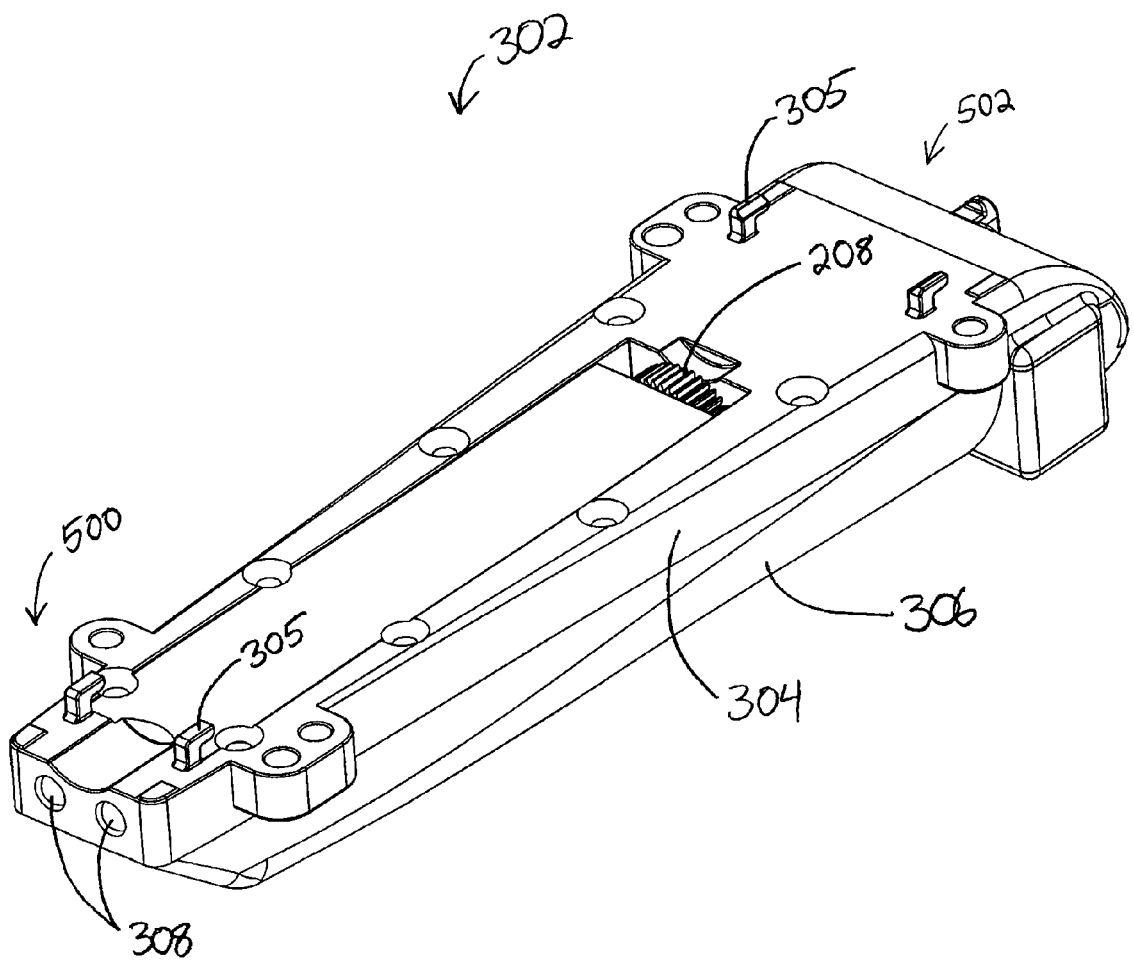
FIG. 16 depicts a front perspective view of a holster of the biopsy device of FIG. 4.
Figure 17:
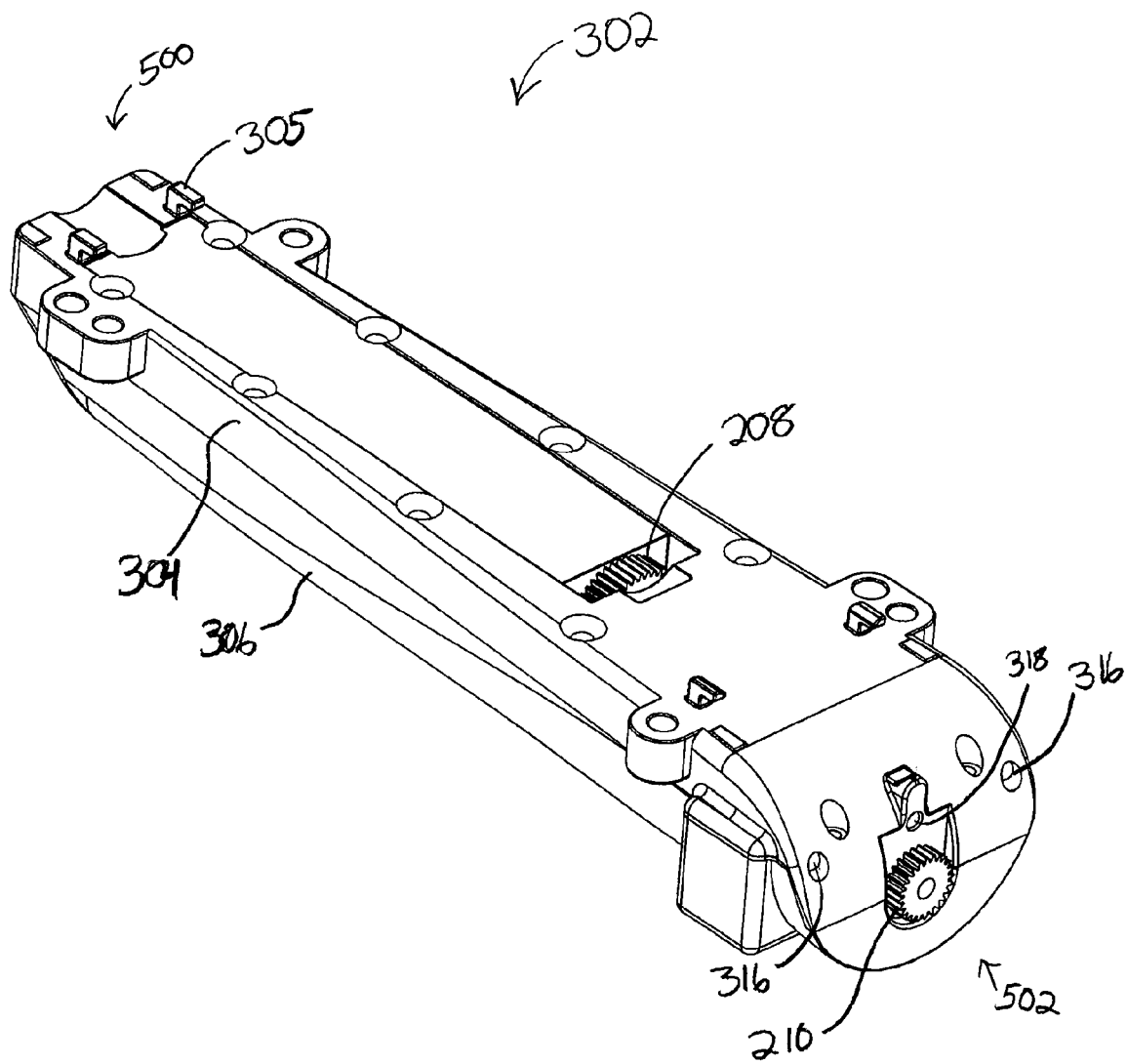
FIG. 17 depicts a rear perspective view of the holster of FIG. 16.

As shown in FIGS. 2-3 and 15, a holster (202) comprises a top cover (204), through which a portion of each of gears (206, 208) is exposed, and side panels (214). Holster (202) of this example further comprises a needle rotation mechanism (not shown), a needle firing mechanism (not shown), a cutter drive mechanism (not shown), and a tissue holder rotation mechanism (not shown). The cutter drive mechanism may be operable to cause the cutter to rotate and translate (e.g., by rotating gear (208) to rotate gear (138)); while the tissue holder rotation mechanism may be operable to cause at least a portion of the tissue sample holder (140) to rotate (e.g., by rotating gear (210) to rotate gear (170)). Suitable components and structures that may be used to provide a cutter drive mechanism and a tissue holder rotation mechanism are disclosed in U.S. Non-Provisional patent application Ser. No. 11/942,764, entitled "Vacuum Timing Algorithm for Biopsy Device," filed Nov. 20, 2007, the disclosure of which is incorporated by reference herein. Of course, any other suitable components, structures, or configurations may be used. Alternatively, either or both of a cutter drive mechanism or a tissue holder rotation mechanism may simply be omitted altogether from a holster (202).

A. Exemplary Needle Rotation Mechanism

In the present example, the needle rotation mechanism of holster (202) comprises a pair of knobs (222). Rotation of one or both of knobs (222) will result in rotation of gear (206). Furthermore, as also noted above, when biopsy probe (102) is coupled with holster (202), gear (206) will mesh with gear (74). Thus, when biopsy probe (102) is coupled with holster (202), rotation of one or both of knobs (222) will cause needle portion (10) of biopsy probe (102) to rotate. Suitable structures and components that may form a needle rotation mechanism are disclosed in U.S. Non-Provisional patent application Ser. No. 11/942,764, entitled "Vacuum Timing Algorithm for Biopsy Device," filed Nov. 20, 2007, the disclosure of which is incorporated by reference herein. Of course, any other suitable components, structures, or configurations may be used. By way of example only, a motor (not shown) may be used to effect rotation of needle portion (10). In other versions, a needle rotation mechanism may simply be omitted altogether.

B. Exemplary Needle Firing Mechanism

A needle firing mechanism of holster (202) the present example comprises a pair of triggers (242), buttons (244), a firing rod (248), and a fork (250). Fork (250) is configured to engage sleeve portion (64) of needle hub (60) when biopsy probe (102) is coupled with holster (202). For instance, fork (250) may engage sleeve portion (64) between thumbwheel (62) and annular projection (66). In the present example, engagement between fork (250) and sleeve portion (64) is such that sleeve portion (64) (and therefore, needle portion (10)) will translate longitudinally and unitarily with fork (250). Fork (250) is coupled with firing rod (248), such that fork (250) will translate longitudinally and unitarily with firing rod (248).

Suitable structures and components that may form a needle firing mechanism, as well as methods of operating a needle firing mechanism, are disclosed in U.S. Non-Provisional patent application Ser. No. 11/942,764, entitled "Vacuum Timing Algorithm for Biopsy Device," filed Nov. 20, 2007, the disclosure of which is incorporated by reference herein. Of course, any other suitable components, structures, configurations, or methods may be used.

III. Exemplary Probe for Ultrasound Use

As shown in FIGS. 4-5, an alternative biopsy probe (103) comprises a needle portion (350) and a body portion (352). A tissue sample holder (368) is removably secured to body portion (352), though tissue sample holder (368) may alternatively be secured to some other component. Like tissue sample holder (140) described above, tissue sample holder (368) includes a cup (142). Biopsy probe (103) is configured to be coupled with a holster (302) to provide a biopsy device (101).

In the present example, needle portion (350) comprises an outer cannula (12) having a tissue piercing tip (14) and a transverse tissue receiving aperture (16), each of which may be configured the same for needle portion (350) as they were described above with respect to needle portion (10). Similarly, cutter (50) in probe (103) may have the same relationship with needle portion (350) as the relationship described above between cutter (50) and needle portion (10); as well as all the same features, properties, and components as cutter (50) described above in the context of probe (102).

A needle hub (358) is secured to outer cannula (12) of probe (103), and comprises a thumbwheel (62) and a sleeve portion (360) extending proximally from thumbwheel (62). Thumbwheel (62) may be used to rotate outer cannula (12) about its longitudinal axis to orient the angular position of aperture (16). However, in the present example, needle hub (358) is not configured to translate longitudinally. In other words, the longitudinal position of needle portion (350) relative to body portion (352) is substantially fixed. Probe (103) is thus configured such that, unlike needle portion (10) of probe (102), needle portion (350) cannot be "fired." Accordingly, since needle portion (350) cannot be fired, some may consider probe (103) to be unsuitable for coupling with holster (202) for use in a stereotactic setting. Probe (103) of this particular example may be considered as being intended for use in a handheld, ultrasound-guided setting, and for coupling only with holster (302) described below.

Probe (103) may also have any of the features, components, and uses described in U.S. Non-Provisional patent application Ser. No. 11/942,764, entitled "Vacuum Timing Algorithm for Biopsy Device," filed Nov. 20, 2007, the disclosure of which is incorporated by reference herein. It should be understood that probe (103) is described herein as being intended for use in a handheld, ultrasound-guided setting, and for coupling only with holster (302), for illustrative purposes only. As will be described in greater detail below, holster (302) may also be configured to be coupled with probe (102), which may render a differently configured probe (103) unnecessary or superfluous.

IV. Exemplary Holster for Ultrasound Use

As shown in FIGS. 4-5 and 16-20, an alternative holster (302) has a distal end (500) and a proximal end (502). Holster (302) further comprises a top housing member (304), through which a portion of each of gears (208, 210) is exposed, and a bottom housing member (306). A plurality of hook members (305) extend from top housing member (304) for selectively securing probe (103) to holster (302), though other structures or techniques may be used. Holster (302) of this example further comprises a cutter drive mechanism (310) and a tissue holder rotation mechanism (320). Each of these merely exemplary components will be described in greater detail below. Holster (302) of the present example is configured to be coupled with a biopsy probe (103), such as biopsy probe (103) described above, to provide a biopsy device (101). In addition, holster (302) is configured to be handheld, such that biopsy device (101) may be manipulated and operated by a single hand of a user (e.g., using ultrasound guidance, etc.). However, it will be appreciated in view of the disclosure herein that holster (302) may be used in a variety of other settings and combinations. By way of example only, holster (302) may alternatively be coupled with biopsy probe (102) instead of biopsy probe (103), as will be described in greater detail below. As another merely illustrative example, holster (302) may be coupled with a variation of biopsy probe (102) that has a modified needle hub (60) (e.g., a needle hub (60) that is shorter, not configured for firing needle portion (10), etc.).

A. Exemplary Cutter Drive Mechanism

Figure 18:
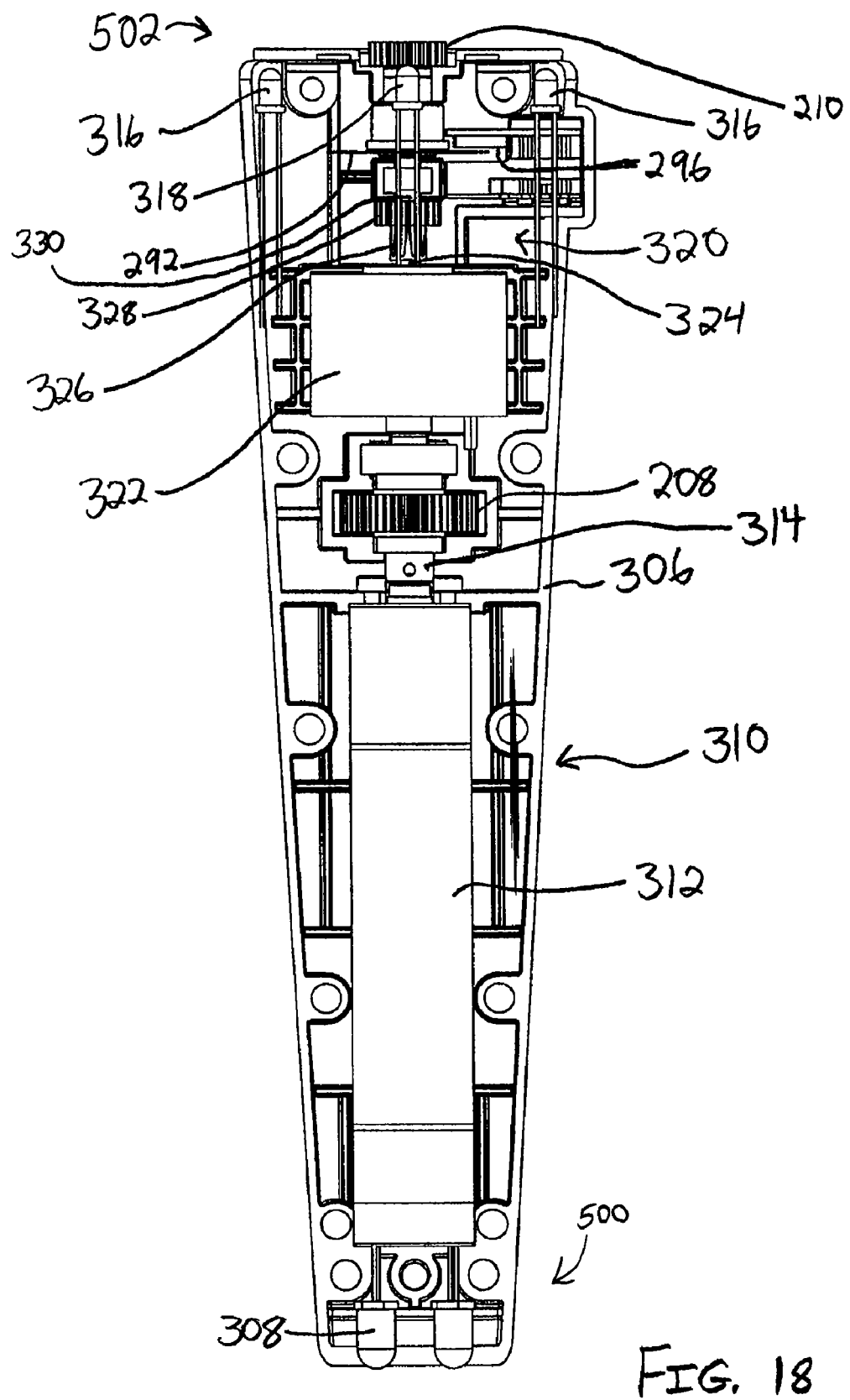
FIG. 18 depicts a top view of the holster of FIG. 16, with a top cover removed.
Figure 19:
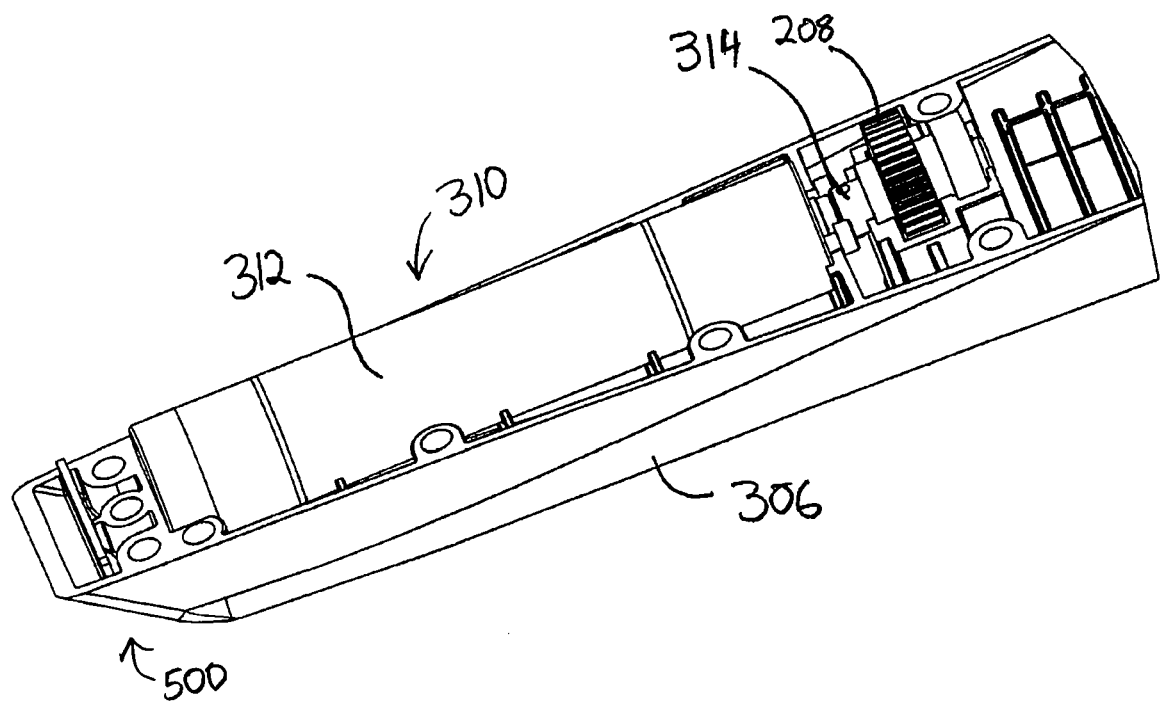
FIG. 19 depicts a partial view of the holster of FIG. 16, showing an exemplary cutter drive mechanism.

As shown in FIGS. 18-19, cutter drive mechanism (310) of the present example comprises a motor (312) with a shaft (314) extending therefrom. Gear (208) is mounted to shaft (314), and is configured to rotate unitarily therewith. As noted above, a portion of gear (208) is exposed through top housing member (304), such that gear (208) meshes with a gear of a cutter rotation and translation mechanism of biopsy probe (103) when biopsy probe (103) is coupled with holster (302). Accordingly, when motor (312) is activated to rotate, such rotation may be communicated via shaft (314) and gears (208), to effect simultaneous rotation and translation of cutter (50). Other ways in which a cutter drive mechanism (310) may be configured or operated will be apparent to those of ordinary skill in the art in view of the teachings herein.

B. Exemplary Tissue Holder Rotation Mechanism

Figure 20:
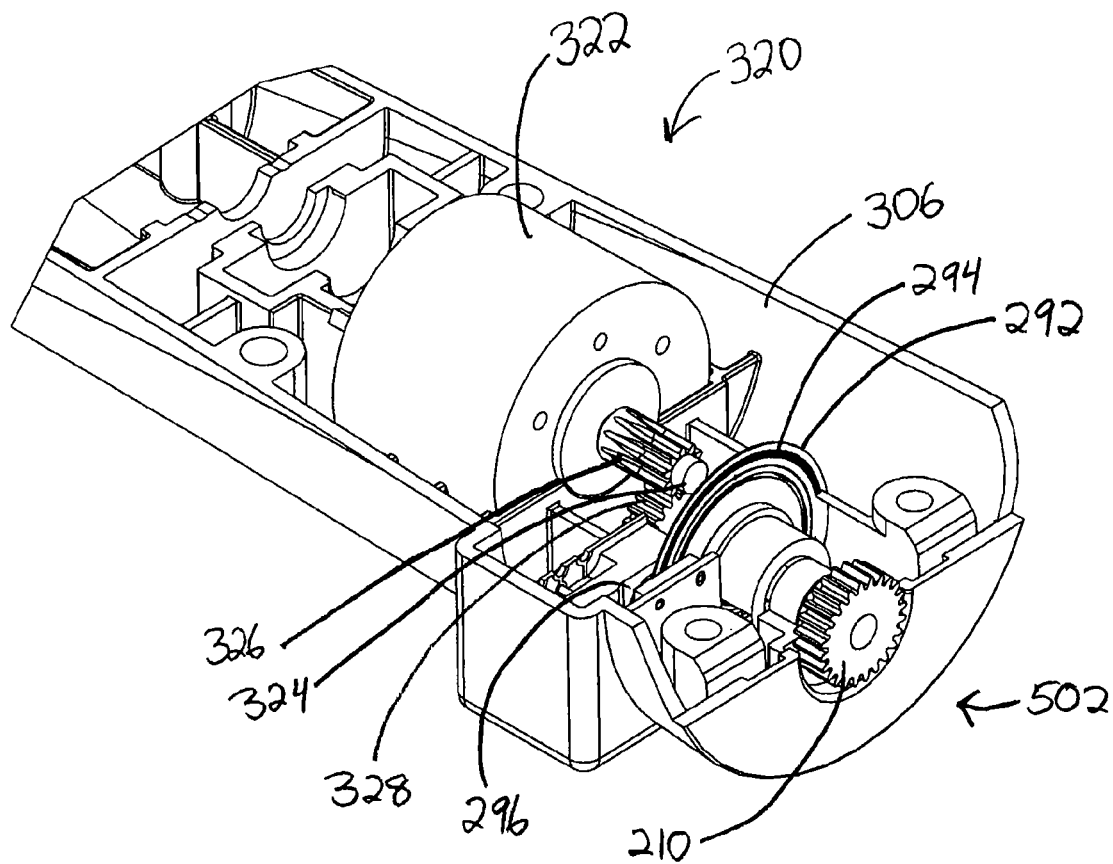
FIG. 20 depicts a partial view of the holster of FIG. 16, showing an exemplary tissue holder rotation mechanism.

As shown in FIGS. 18 and 20, tissue holder rotation mechanism (320) of the present example comprises a motor (322) having a shaft (324) with a gear (326) mounted thereto, such that gear (326) rotates unitarily with shaft (324). Gear (326) is configured to mesh with gear (328), which is mounted to shaft (330). Gear (210), which has been noted above, is also mounted to shaft (330), at the proximal end of shaft (330). In particular, gear (210) is configured to mesh with a gear (not shown) of tissue sample holder (368) of biopsy probe (103) when biopsy probe (103) is coupled with holster (302). Accordingly, when motor (322) is activated to rotate, such rotation may be communicated via shafts (324, 330) and gears (326, 328, 210), to effect rotation of a manifold (not shown) within tissue sample holder (368) for indexing tissue sample chambers.

In addition, an encoder wheel (292) is coupled with shaft (330), and is configured to rotate unitarily therewith. Encoder wheel (292) has a plurality of radially extending slots (294) formed therethrough. A sensor (296) is positioned adjacent to encoder wheel (292). In particular, sensor (296) is positioned such that slots (294) successively pass before sensor (296) as encoder wheel (292) rotates with shaft (290). Sensor (296) may therefore be used to count the passage of slots (294), which may be translated into rotational position of a rotatable manifold within tissue sample holder (368). In other words, since encoder wheel (292) and the manifold rotate concomitantly when biopsy probe (103) is coupled with holster (302) in the present example, the passage of slots (294) past sensor (296) during rotation of shaft (330) may be indicative of manifold rotation, and therefore of manifold position. It will be appreciated that such information may be further indicative of which particular tissue sample chamber of tissue sample holder (368) is aligned with cutter lumen (52). Suitable uses for such information will be apparent to those of ordinary skill in the art in view of the teachings herein. Suitable devices that may be used for sensor (296) will also be apparent to those of ordinary skill in the art in view of the teachings herein. Furthermore, other ways in which a tissue holder rotation mechanism (320) may be configured or operated will be apparent to those of ordinary skill in the art in view of the teachings herein.

Holster (302) may also include a variety of other features, including but not limited to a plurality of LEDs (308, 316, 318). Other suitable components, features, and variations that may be incorporated into a holster (302) are disclosed in U.S. Non-Provisional patent application Ser. No. 11/942,764, entitled "Vacuum Timing Algorithm for Biopsy Device," filed Nov. 20, 2007, the disclosure of which is incorporated by reference herein.

C. "Universal" Probe

As described above, probe (103) is configured to be coupled with holster (302), and vice versa; while probe (102) is configured to be coupled with holster (202), and vice versa. In other words, in some versions, the pair of probe (103) and holster (302) may be regarded as intended for use in a handheld, ultrasound-guided setting; while the pair of probe (102) and holster (302) may be regarded as intended for use in a fixture-based, stereotactic setting. Thus, in some versions, probe (103) is not intended to be coupled with holster (202); and probe (102) is not intended to be coupled with holster (302). Of course, probes (102, 103) and holsters (202, 302) may alternatively be used in any desired combination and in any desired setting.

Any of probes (102, 103) and/or holsters (202, 302) may be modified to permit effective coupling of probe (103) with holster (202); and/or to permit effective coupling of probe (102) with holster (302). In other words, either of the above probes (102, 103) may be regarded as a "universal" probe, such that the probe (102, 103) may be effectively coupled with either type of holster (202, 302), as desired. While the below example discusses probe (102) as a "universal" probe, it will be appreciated that any other type of probe may be provided as a "universal" probe (102), including but not limited to probe (103). In addition, while the below example discusses a modification of holster (302) to effectively accommodate a universal probe (102), holster (202) and/or any version of probe (102, 103) may be subject to any desired form(s) of modification to provide effective accommodation between any of these components.

Figure 21:
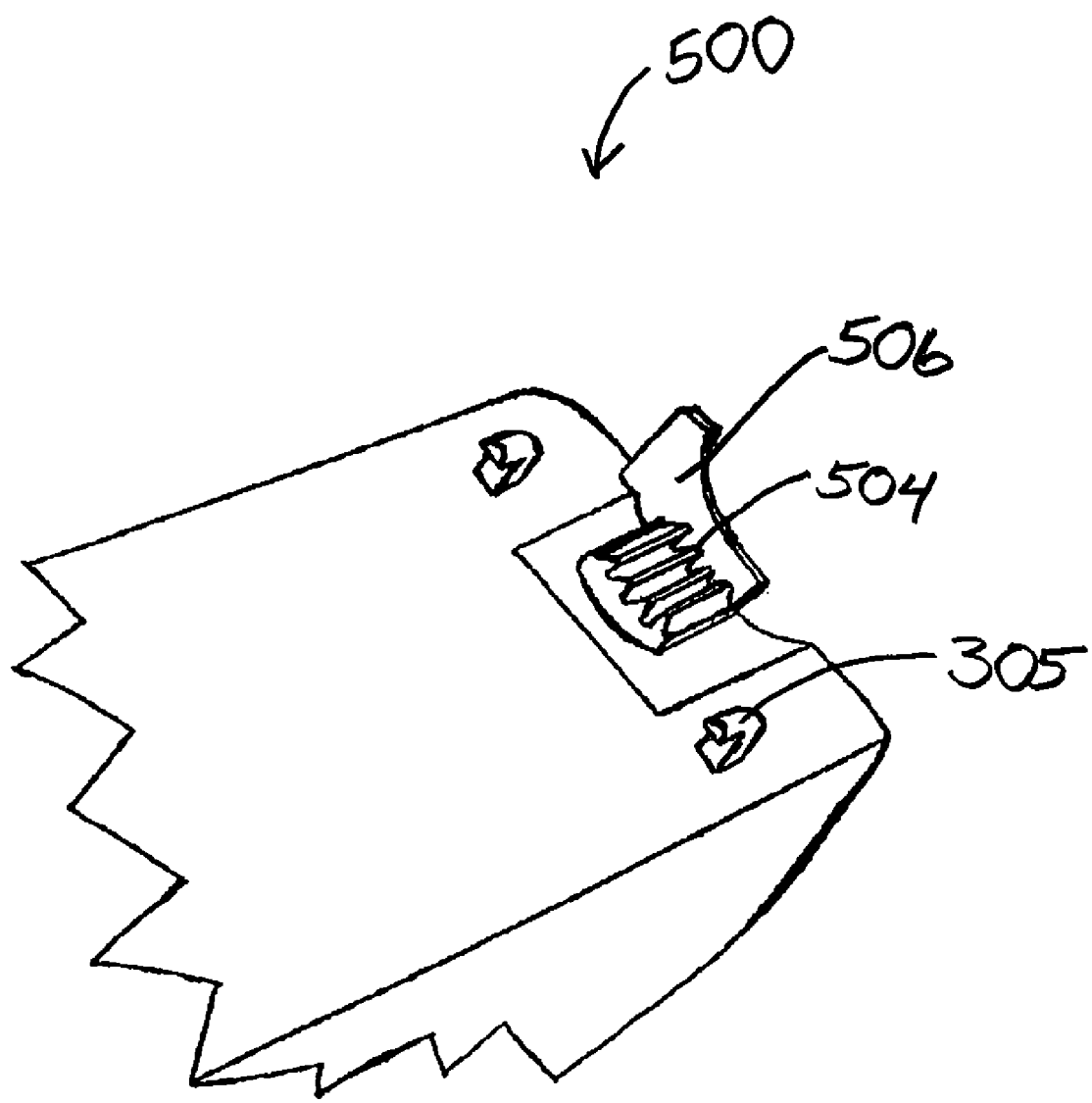
FIG. 21 depicts a perspective view of an exemplary variation of the distal end of the holster of FIG. 16

As shown in FIG. 21, the distal end (500) of holster (302) may be modified to accommodate probe (102). In particular, the distal end (500) of holster may include a set of rigid locking teeth (504) that are configured to engage teeth of gear (74) upon coupling of probe (102) with holster (302). Teeth (504) may be integrally formed with top housing member (304). For instance, in some versions, top housing member (304) comprises a molded plastic, and teeth (504) are molded as a unitary part of top housing member (304) (e.g., such that teeth (504) and the remainder of top housing member (304) form a homogenous continuum of material). Of course, teeth (504) may be provided in a variety of other ways. By way of example only, teeth (504) may be part of an adapter (not shown) that is configured to selectively engage distal end (500) of holster (302) (e.g., by snapping on, by clamping on, etc.). In some such variations, holster (302) may be configured to accept probe (103) in the absence of the adapter; while being configured to accept probe (102) when the adapter is coupled with holster (302). Still other ways in which teeth (504) may be provided will be apparent to those of ordinary skill in the art in view of the teachings herein. It will also be appreciated that any other suitable structures or devices may be used in addition to or in lieu of teeth (504), as desired.

As described above, gear (74) is operable to rotate needle portion (10) of probe (102). To the extent that gear (74) is prevented from rotating, needle portion (10) will also be prevented from rotating. In the present example, because teeth (504) are integral with top housing member (304), engagement of teeth (504) with teeth of gear (74) will prevent gear (74) from rotating. Teeth (504) will thus prevent needle portion (10) from rotating when probe (102) is coupled with holster (302).

As is also shown in FIG. 21, the distal end (500) of holster (302) may be modified to include a projection (506). Projection (506) may be configured to engage a portion of needle hub (60) when probe (102) is coupled with holster (302). Like teeth (504), projection (506) may be integrally formed with top housing member (304). For instance, in some versions, top housing member (304) comprises a molded plastic, and projection (506) is molded as a unitary part of top housing member (304) (e.g., such that projection (506) and the remainder of top housing member (304) form a homogenous continuum of material). Of course, projection (506) may be provided in a variety of other ways. By way of example only, projection (506) may be part of an adapter (not shown) that is configured to selectively engage distal end (500) of holster (302) (e.g., by snapping on, by clamping on, etc.). In some such variations, holster (302) may be configured to accept probe (103) in the absence of the adapter; while being configured to accept probe (102) when the adapter is coupled with holster (302). Still other ways in which projection (506) may be provided will be apparent to those of ordinary skill in the art in view of the teachings herein. It will also be appreciated that any other suitable structures or devices may be used in addition to or in lieu of projection (506), as desired.

Engagement of projection (506) with a portion of needle hub (60) may operate to prevent needle hub (60) from moving longitudinally along the axis defined by needle portion (10). In the present example, to the extent that needle hub (60) is prevented from translating longitudinally, the remainder of needle portion (10) is also prevented from translating longitudinally. Thus, when probe (102) is coupled with holster (302), such projection (506) may prevent needle portion (10) from translating longitudinally. While needle portion (10) may translate longitudinally when coupled with probe (202) to effect "firing" of needle portion (10); projection (506) may essentially disable the firing capabilities of needle portion (10) when probe (102) is coupled with holster (302).

By way of example only, projection (506) may be configured to engage the distal face of thumbwheel (62), such that engagement between projection (506) and thumbwheel (62) prevents needle portion (10) from translating longitudinally. In other versions, projection (506) may be configured to engage the distal face of annular projection (66) of sleeve portion (64), such that engagement between projection (506) and annular projection (66) prevents needle portion (10) from translating longitudinally. In some other versions, sleeve portion (64) may include an annular recess (not shown) configured to receive a portion of projection (506), such that engagement between projection (506) and the recess prevents needle portion (10) from translating longitudinally. Alternatively, projection (506) may be configured to engage any other portion of needle hub (60), any other portion of needle portion (10), or any other structure in order to prevent needle portion (10) from translating longitudinally. Again, though, any other suitable structures or devices may be used in addition to or in lieu of projection (506), as desired.

In a merely exemplary use of probe (102) with a modified version of holster (302), a user may rotate needle portion (10) relative to body portion (112) of probe (102) to achieve a desired angular orientation of aperture (16) before coupling probe (102) with holster (302). Upon reaching the desired angular orientation of aperture (16), the user may then couple probe (102) with holster (302). Engagement between teeth (504) and teeth of gear (74) may "lock" the rotational position of needle portion (10), thereby maintaining the desired angular orientation of aperture (16) for use. To the extent that needle portion (10) is configured to translate longitudinally before probe (102) is coupled with holster (302), the user may set the longitudinal position of needle portion (10) relative to body portion (112) to a position that permits effective engagement between projection (506) and some component that is integral with needle portion (10) (e.g., needle hub (60)). For instance, in some versions, the user may need to pull the needle portion (10) back in the proximal direction as far as it will go before the longitudinal position of needle portion (10) relative to body portion (112) is in a position that permits effective engagement between projection (506) and some component that is integral with needle portion (10). In other versions, probe (102) may be configured such that projection (506) effectively engages a component that is integral with needle portion (10) when needle portion (10) is at a variety of longitudinal positions (or any longitudinal position) relative to body portion (112) upon coupling of probe (102) with holster (302).

To the extent that a user desires to obtain biopsy samples using a variety of angular orientations of aperture (16) during a single biopsy session, the user may decouple probe (102) from holster (302) to permit needle portion (10) to be rotated to change the orientation of aperture (16), then re-couple probe (102) with holster (302) to "lock" the new angular orientation of aperture (16). This process may be repeated until biopsy samples are taken using every angular orientation of aperture (16) desired. To adjust the angular orientation of aperture (16) when probe (102) is decoupled from holster (302), the user may simply grip thumbwheel (62) with their hand to rotate needle portion (10) manually.

Of course, probe (102) and holster (302) (modified or otherwise) may be used in a variety of other ways, as desired.

In some other variations of holster (302), a fork (not shown) or other structure is provided in addition to or in lieu of teeth (504) and/or projection (506). Such a fork may have some characteristics similar to fork (250) described above. For instance, a fork on holster (302) may be configured to engage sleeve portion (64), between annular projection and thumbwheel (62), similar to fork (250) described above. A fork on holster (302) may thus prevent needle portion (10) from moving longitudinally relative to body portion (112) upon coupling of probe (102) with holster (302). In other words, a fork may serve as a substitute for projection (506). Still other ways in which a fork or other structure may be used to prevent longitudinal movement of needle portion (10) relative to body portion (112) when probe (102) is coupled with holster (302), including modifications to probe (102) to effectively engage such a fork, will be apparent to those of ordinary skill in the art in view of the teachings herein.

In addition or in the alternative, a fork on holster (302) may serve as a substitute for teeth (504). By way of example only, a fork may be configured to grip or otherwise engage a portion of needle hub (60) to prevent needle hub (60) from rotating relative to body portion (112). For instance, a fork of holster (302) may be configured to grip or otherwise engage thumbwheel (62) to prevent thumbwheel (62) from rotating, which may thereby prevent needle portion (10) from rotating relative to body portion (112). Alternatively, sleeve portion (64) may include one or more flats that are configured to engage prongs of a fork extending from holster (302), such that engagement between the prongs and the flats prevent rotation of needle portion (10) relative to body portion (112) when probe (102) is coupled with holster (302). Still other ways in which a fork or other structure may be used to prevent rotation of needle portion (10) relative to body portion (112) when probe (102) is coupled with holster (302), including modifications to probe (102) to effectively engage such a fork, will be apparent to those of ordinary skill in the art in view of the teachings herein.

A fork is merely one alternative structure that may be used in addition to or in lieu of teeth (504) and/or projection (506). Still other suitable structures and devices that may be used, regardless of whether such structures are incorporated into probe (102) and/or holster (302), will be apparent to those of ordinary skill in the art in view of the teachings herein.

V. Exemplary Vacuum Control Module and Canister

Either biopsy device (100, 101) may be coupled with a vacuum control module (400) that is operable to provide fluids (e.g., vacuum, atmospheric air, saline, pressurized air, etc.), power, and/or commands to biopsy device (100, 101). Suitable examples of such a vacuum control module (400), as well as ways in which fluids may be selectively communicated to a biopsy device (100, 101) and ways in which a biopsy device (100, 101) may be operated, are disclosed in U.S. Non-Provisional patent application Ser. No. 11/942,764, entitled "Vacuum Timing Algorithm for Biopsy Device," filed Nov. 20, 2007, the disclosure of which is incorporated by reference herein. Of course, any other suitable components, structures, or configurations may be used.

Alternatively, biopsy device (100, 101) may be provided and used without a vacuum control module (400). By way of example only, biopsy device (100, 101) may have an on-board vacuum pump (not shown) and/or pressure pump (not shown). Merely exemplary biopsy devices with such on-board pumps are disclosed in U.S. Non-Provisional patent application Ser. No. 11/965,048, filed Dec. 27, 2007, entitled "Vacuum Sensor and Pressure Pump for Tetherless Biopsy Device," the disclosure of which is incorporated by reference herein; and in U.S. Non-Provisional patent application Ser. No. 11/964,811, filed Dec. 27, 2007, entitled "Clutch and Valving System for Tetherless Biopsy Device," the disclosure of which is incorporated by reference herein. Again, though, any other suitable components, structures, or configurations may be used.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy device, wherein the biopsy device comprises:
   (a) a biopsy probe, wherein the biopsy probe comprises:
      (i) a needle having a tissue piercing tip and a tissue receiving aperture proximal to the tip,
      (ii) a cutter operable to translate relative to the needle to sever tissue protruding through the aperture, and
      (iii) a body portion, wherein the needle is rotatable relative to the body portion; and
   (b) a holster, wherein the probe is configured to couple with the holster, wherein the holster comprises a first locking feature configured to engage a portion of the probe, wherein the first locking feature is configured to prevent the needle from rotating relative to the body portion upon coupling of the probe with the holster, wherein the first locking feature is fixedly attached to the holster.

2. The biopsy device of claim 1, wherein the probe further comprises a gear and an opening, wherein at least a portion of the gear is exposed through the opening, wherein the gear is configured to rotate with the needle.

3. The biopsy device of claim 2, wherein the first locking feature is configured to engage the gear of the probe to prevent the needle from rotating relative to the body portion upon coupling of the probe with the holster.

4. The biopsy device of claim 3, wherein the first locking feature comprises a plurality of teeth.

5. The biopsy device of claim 1, wherein the holster comprises a housing, wherein the first locking feature is integral with the housing.

6. The biopsy device of claim 5, wherein the housing has an upper surface, wherein the first locking feature extends from the upper surface of the housing.

7. The biopsy device of claim 1, wherein the needle is further configured to translate longitudinally relative to the body portion.

8. The biopsy device of claim 7, wherein the first locking feature is further configured to prevent the needle from translating longitudinally relative to the body portion upon coupling of the probe with the holster.

9. The biopsy device of claim 7, wherein the holster further comprises a second locking feature, wherein the second locking feature is configured to prevent the needle from translating longitudinally relative to the body portion upon coupling of the probe with the holster.

10. The biopsy device of claim 9, wherein the second locking feature comprises a projection extending outward relative to a portion of the holster.

11. The biopsy device of claim 10, wherein the holster comprises a housing, wherein the projection extends outwardly from the housing.

12. The biopsy device of claim 9, wherein the holster has a proximal end and a distal end, wherein the needle extends distally relative to the distal end of the holster when the probe is coupled with the holster, wherein the second locking feature is positioned at the distal end of the holster.

13. The biopsy device of claim 9, wherein the needle further comprises an annular projection, wherein the second locking feature is configured to engage the annular projection to prevent the needle from translating longitudinally relative to the body portion upon coupling of the probe with the holster.

14. The biopsy device of claim 1, wherein the holster has a proximal end and a distal end, wherein the needle extends distally relative to the distal end of the holster when the probe is coupled with the holster, wherein the first locking feature is positioned at the distal end of the holster.

15. A biopsy device, wherein the biopsy device comprises:
(a) a biopsy probe, wherein the biopsy probe comprises:
    (i) a needle having a tissue piercing tip and a tissue receiving aperture proximal to the tip,
    (ii) a cutter operable to translate relative to the needle to sever tissue protruding through the aperture, and
    (iii) a body portion, wherein the needle is translatable relative to the body portion; and
(b) a holster, wherein the probe is configured to couple with the holster, wherein the holster comprises a locking feature configured to engage a portion of the probe, wherein the locking feature is configured to prevent the needle from translating relative to the body portion upon coupling of the probe with the holster, wherein the locking feature is an integrally formed part of the holster.

16. The biopsy device of claim 15, wherein the needle is rotatable relative to the body portion, wherein the locking feature is further configured to prevent the needle from rotating relative to the body portion upon coupling of the probe with the holster.

17. The biopsy device of claim 16, wherein the locking feature comprises a set of teeth and a projection separate from the teeth.

18. A method of combining a biopsy probe with a holster to provide a biopsy device, wherein the biopsy probe comprises a needle, a cutter, and a body portion, wherein the needle has a tissue piercing tip and a tissue receiving aperture proximal to the tip, wherein the cutter is operable to translate relative to the needle to sever tissue protruding through the aperture, wherein the needle is rotatable relative to the body portion, wherein the holster comprises a locking feature configured to engage a portion of the probe, wherein the locking feature is configured to prevent the needle from rotating relative to the body portion upon coupling of the probe with the holster, and wherein the locking feature is fixed relative to the holster, the method comprising:
(a) adjusting the angular orientation of the tissue receiving aperture by rotating the needle about an axis defined by the needle to reach a selected angular orientation; and
(b) coupling the probe with the holster to lock the selected angular orientation with the locking feature, wherein the locking feature prevents any rotation of the needle for the entire duration of the biopsy probe being coupled with the holster.

19. The method of claim 18, wherein the needle is further configured to translate relative to the body portion, wherein the locking feature is further configured to engage a portion of the probe to prevent the needle from translating relative to the body portion upon coupling of the probe with the holster.

20. The method of claim 18, wherein the needle comprises a gear having teeth, wherein the locking feature comprises teeth, wherein the act of coupling the probe with the holster comprises engaging the teeth of the gear with the teeth of the locking feature.

* * * * *